US012290391B2

(12) United States Patent
Zhou et al.

(10) Patent No.: US 12,290,391 B2
(45) Date of Patent: May 6, 2025

(54) LOW DOSE CORONARY CALCIUM SCORING AT LOW AND STANDARD TUBE POTENTIALS

(71) Applicant: Cedars-Sinai Medical Center, Los Angeles, CA (US)

(72) Inventors: Yifang Zhou, Irvine, CA (US); Di Zhang, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 210 days.

(21) Appl. No.: 18/052,725

(22) Filed: Nov. 4, 2022

(65) Prior Publication Data

US 2023/0097215 A1 Mar. 30, 2023

Related U.S. Application Data

(63) Continuation-in-part of application No. PCT/US2021/030448, filed on May 3, 2021.
(Continued)

(51) Int. Cl.
*A61B 6/50* (2024.01)
*A61B 6/00* (2006.01)
*A61B 6/03* (2006.01)

(52) U.S. Cl.
CPC .............. *A61B 6/503* (2013.01); *A61B 6/032* (2013.01); *A61B 6/504* (2013.01); *A61B 6/56* (2013.01)

(58) Field of Classification Search
CPC ......... A61B 6/503; A61B 6/032; A61B 6/504; A61B 6/56
See application file for complete search history.

(56) References Cited

U.S. PATENT DOCUMENTS 10,339,634 B2 * 7/2019 Wang .................... G06T 11/006
2007/0140428 A1 * 6/2007 Toth ........................ A61B 6/542
378/108
(Continued)

FOREIGN PATENT DOCUMENTS

WO WO-2018213808 A1 * 11/2018 ......... A61B 5/02007

OTHER PUBLICATIONS

International Search Report and Written Opinion International Application No. PCT/US21/30448, mailed Aug. 13, 2021, pp. 11.
(Continued)

*Primary Examiner* — Dani Fox
*Assistant Examiner* — Mamadou Faye
(74) *Attorney, Agent, or Firm* — NIXON PEABODY LLP

(57) ABSTRACT

A dose for a coronary calcium scoring (CCS) computed tomography (CT) scan (e.g., a volume CT dose index (CTDIvol)) can be determined for lower tube voltages (e.g., a lower peak kilovoltage (kVp)) based on a given reference tube voltage. A dose lookup table can be created and used to determine appropriate dosing for CCS while operating at lower kVp based on a reference kVp. This dose lookup table can be created specifically to achieve a consistent contrast-to-noise (CNR) ratio. Additionally, certain aspects and features of the present disclosure also relate to a kVp-dependent scaling method to process images so standard CCS software can be used with standard Houndsfield unit (HU) thresholds. Images captured at non-standard kVp can be processed according to the disclosed scaling method prior to being transferred to CCS software for scoring based on a presumed standard kVp.

20 Claims, 22 Drawing Sheets

Related U.S. Application Data

(60) Provisional application No. 63/131,580, filed on Dec. 29, 2020, provisional application No. 63/019,541, filed on May 4, 2020.

(56) References Cited

U.S. PATENT DOCUMENTS

| | | | |
|---|---|---|---|
| 2007/0258559 A1* | 11/2007 | Hur | A61B 6/583 378/109 |
| 2011/0213242 A1 | 9/2011 | Budoff | |
| 2012/0114093 A1* | 5/2012 | Yu | A61B 6/481 378/8 |

OTHER PUBLICATIONS

Zhang et al., Coronary artery calcium scoring at lower tube voltages—Dose determination and scoring mechanism, European Journal of Radiology, vol. 139, 2021, Article 109667, pp. 10.

* cited by examiner

LOW DOSE CORONARY CALCIUM SCORING AT LOW AND STANDARD TUBE POTENTIALS

CROSS REFERENCE TO RELATED APPLICATIONS

This application is a continuation-in-part of International Application No. PCT/US2021/030448, filed May 3, 2021, which claims priority to and the benefit of U.S. Provisional Patent Application No. 63/131,580, filed Dec. 29, 2020, and U.S. Provisional Patent Application No. 63/019,541, filed May 4, 2020, each of which is hereby incorporated by reference in its entirety.

TECHNICAL FIELD

The present disclosure relates to medical imaging generally and more specifically to improvements in capturing and analyzing coronary calcification.

BACKGROUND

Heart disease remains a leading cause of death among many populations. For certain populations of individuals at intermediate or borderline risk of atherosclerotic cardiovascular disease (ASCVD), such as if risk-based decisions for preventive interventions (e.g., statin therapy) remain uncertain, it can be useful to measure a coronary artery calcium score to guide clinician-patient risk discussion and further monitoring and/or treatment.

Coronary calcium scoring (CCS) is a useful approach for cardiac risk prognostication. CCS involves using a computed tomography (CT) scan to detect plaque or calcium build-up in and/or around the heart, such as in coronary arteries. Since CCS relies on CT scans, each scan results in dosing the patient with ionizing radiation. While ionizing radiation can be used for important and beneficial reasons, exposure to this radiation can carry small, albeit nonzero, risks. Therefore, a desire exists to achieve successful CSS with a dose as low as reasonably achievable.

Current standard techniques for CCS perform CT scans at a peak kilovoltage (kVp) of 120 kilovolts (kV) with a volume CT dose index ($CTDI_{vol}$) of approximately 3 milligray (mGy) and a dose-length product (DLP) of approximately 50 mGy*cm for patients of average size. The dose is higher for patients of large size. The resultant image can be analyzed to calculate a score based on the extent of coronary artery calcification. Standard techniques involve the calculation of an Agatston score, which is a weighted density score given to the highest attenuation value multiplied by the area of the calcification speck. More specifically, the measured calcium density in Hounsfield units (HU) of the highest density of calcification in a given coronary artery region is assigned a first score (e.g., a density factor) based on accepted thresholds. The accepted Hounsfield unit thresholds include densities of 0-129 HU assigned a score of 0; densities of 130-199 HU assigned a score of 1; densities of 200-299 HU assigned a score of 2; densities of 300-399 HU assigned a score of 3; and densities of 400 HU or more assigned a score of 4. This first score can be multiplied by the area of the coronary calcification (e.g., in square millimeters), which can then be added to the scores from other areas of the CT scan, including other slices, to obtain a total coronary artery calcium score (CAC score), which is the Agatston score. A CAC score of 0 can indicate no evidence of coronary artery disease (CAD), a CAC score of 1-10 can indicate minimal CAD, a CAC score of 11-100 can indicate mild CAD, a CAC score of 101-400 can indicate moderate CAD, and a CAC scores of greater than 400 can indicate severe CAD.

Since adjustments to the kVp result in radiographic contrast changes, standard techniques for reducing dose primarily rely on adjustment to the tube current and exposure time. Other approaches to performing CCS using lower kVp have been attempted, but have been unsuccessful, at least in part due to the lack of a consistent methodology to determine correct dosing for adequate calcium scoring, and because of degradation in the resultant image quality. For example, as kVp lowered, the resultant image can show false calcifications due to the change in radiographic contrast. Overall, existing techniques to reduce dose have been unsuccessful, empirical, and inconsistent. Current techniques have simply been unable to reliably produce successful CCS at appropriate lower dose in general. Therefore, there is a need for improved CCS techniques to further lower dose while maintaining reliable and accurate coronary calcium scoring.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure relate to a method for measuring cardiac health, the method comprising: determining a target peak kilovoltage for driving a radiation source of a medical scanner, wherein the target peak kilovoltage is less than 120 kV; determining an appropriate dose based on the target peak kilovoltage, wherein the appropriate dose is determined to achieve a contrast-to-noise ratio equal to a contrast-to-noise ratio associated with a defined target peak kilovoltage of 120 kV; determining dose parameters based on the appropriate dose; and driving the medical scanner using the target peak kilovoltage and the dose parameters.

In some cases, the target peak kilovoltage is at or between 70 kV and 100 kV. In some cases, the medical scanner is a computed tomography (CT) scanner. In some cases, determining the appropriate dose comprises applying a reducing factor to a reference dose, wherein the reference dose is associated with the defined target peak kilovoltage of 120 kV. In some cases, determining the appropriate dose comprises applying the formula $$CTDI_{vol} = \left(\frac{kVp_{target}}{120}\right)^{1.246} * CTDI_{vol,ref}$$

where $CTDI_{vol}$ is the appropriate dose in mGy, kVptarget is the target peak kilovoltage in kV, and $CTDI_{vol,ref}$ is the reference dose in mGy at 120 kVp. In some cases, driving the medical scanner comprises generating radiation at the radiation source and directing the radiation through target tissue. In some cases, the target tissue comprises calcifications in a coronary artery.

In some cases, the method further comprises receiving scanner data associated with driving the medical scanner using the target peak kilovoltage and the dose parameters; and scaling the scanner data based on the target peak kilovoltage. In some cases, the method further comprises analyzing the scaled scanner data using standard Hounsfield unit thresholds to calculate an Agatston score associated with the scanner data. In some cases, the standard Hounsfield unit (HU) thresholds comprise a first threshold of 0-129 HU associated with a score of 0, a second threshold of 130-199 HU associated with a score of 1, a third threshold of 200-299 HU associated with a score of 2, a third threshold of 300-399 HU associated with a score of 3, and a fourth threshold of 400 HU or greater associated with a score of 4. In some cases, scaling the scanner data comprises: determining a scaling factor using the target peak kilovoltage; and scaling each pixel of the scanner data by the scaling factor. In some cases, determining the scaling factor comprises applying the target peak kilovoltage to a lookup table. In some cases, the scaling factor is at or approximately 1.59 when the peak kilovoltage is 70 kV, the scaling factor is at or approximately 1.38 when the peak kilovoltage is 80 kV, the scaling factor is at or approximately 1.24 when the peak kilovoltage is 90 kV, and the scaling factor is at or approximately 1.14 when the scaling factor is 100 kV.

Embodiments of the present disclosure relate to a method for pre-processing data for coronary calcium scoring, the method comprising: receiving scanner data associated with driving a computed tomography (CT) scanner at a target peak kilovoltage below 120 kV; determining a scaling factor using the target peak kilovoltage; scaling each pixel of the scanner data by the scaling factor; and outputting the scaled scanner data, wherein the scaled scanner data is analyzable using standard Hounsfield unit thresholds to calculate an Agatston score associated with the scanner data.

In some cases, the standard Hounsfield unit (HU) thresholds comprise a first threshold of 0-129 HU associated with a score of 0, a second threshold of 130-199 HU associated with a score of 1, a third threshold of 200-299 HU associated with a score of 2, a third threshold of 300-399 HU associated with a score of 3, and a fourth threshold of 400 HU or greater associated with a score of 4. In some cases, the scaling factor is at or approximately 1.59 when the peak kilovoltage is 70 kV, the scaling factor is at or approximately 1.38 when the peak kilovoltage is 80 kV, the scaling factor is at or approximately 1.24 when the peak kilovoltage is 90 kV, and the scaling factor is at or approximately 1.14 when the scaling factor is 100 kV.

Embodiments of the present disclosure relate to a method of measuring cardiac health comprising determining a noise threshold $\sigma_t$ for a scan, the noise threshold $\sigma_t$ being based at least in part on a size of the subject; determining an optimal dose $CTDI_{vol,opt}$ based at least in part on the noise threshold $\sigma_t$; and determining dose parameters based at least in part on the optimal dose $CTDI_{vol,opt}$.

In some cases, the noise threshold $\sigma_t$ is based at least in part on the size of the subject relative to one or more threshold sizes. In some cases, the noise threshold $\sigma_t$ is based at least in part on the size of the subject relative to a first threshold size and a second threshold size. In some cases, the size of the subject is an effective diameter of a chest of the subject, the first threshold size is 30 centimeters, and the second threshold size is 36 centimeters. In some cases, the noise threshold $\sigma_t$ has a first value if the size of the subject is less than or equal to the first threshold size, a second value if the size of the subject is greater than or equal to the first threshold size and less than or equal to the second threshold size, and a third value if the size of the subject is greater than the second threshold size.

In some cases, determining the noise threshold $\sigma_t$ includes applying the formula $\sigma_t=$ $$\begin{cases} \sigma_{t1}, & \text{if } d_h \leq d_{h1} \\ Ke^{\lambda D_h}, & \text{if } d_{h1} \leq d_h \leq d_{h2} \\ Ke^{\lambda D_h}(\text{option 1}), & \text{if } d_h > d_{h2} \\ \sigma_{t2}(\text{option 2}), & \text{if } d_h > d_{h2} \end{cases},$$

where K and $\lambda$ are constants with known values, $d_{h1}$ is the first threshold size, $d_{h2}$ is the second threshold size, and $d_h$ is the size of the subject. In some cases, determining the optimal dose $CTDI_{vol,opt}$ includes applying the formula $$CTDI_{vol,opt} = \left(\frac{Ae^{Bq(D_h)}}{\sigma_t}\right)^{-\frac{1}{C}},$$

where A, B, and C are constants with known values, and $q(D_h)$ is a function that represents the size of the of the subject relative to a reference size.

In some cases, the medical scan is used to determine a coronary artery calcium score for the subject. In some cases, the method further comprises driving a medical scanner using the dose parameters and a peak kilovoltage of 120 kV to perform the medical scan. In some cases, the dose parameters include a tube current and an exposure time. In some cases, the medical scanner is a computed tomography (CT) scanner.

Embodiments of the present disclosure further relate to a system comprising: a control system including one or more processors; and a memory having stored thereon machine readable instructions; wherein the control system is coupled to the memory, and any one of the methods described above is implemented when the machine executable instructions in the memory are executed by at least one of the one or more processors of the control system.

Embodiments of the present disclosure further relate to a system for assessing coronary artery calcification, the system including a control system configured to implement any one of the methods described above.

Embodiments of the present disclosure further relate to a computer program product comprising instructions which, when executed by a computer, cause the computer to carry out any one of the methods described above. In some cases, the computer program product is a non-transitory computer readable medium.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
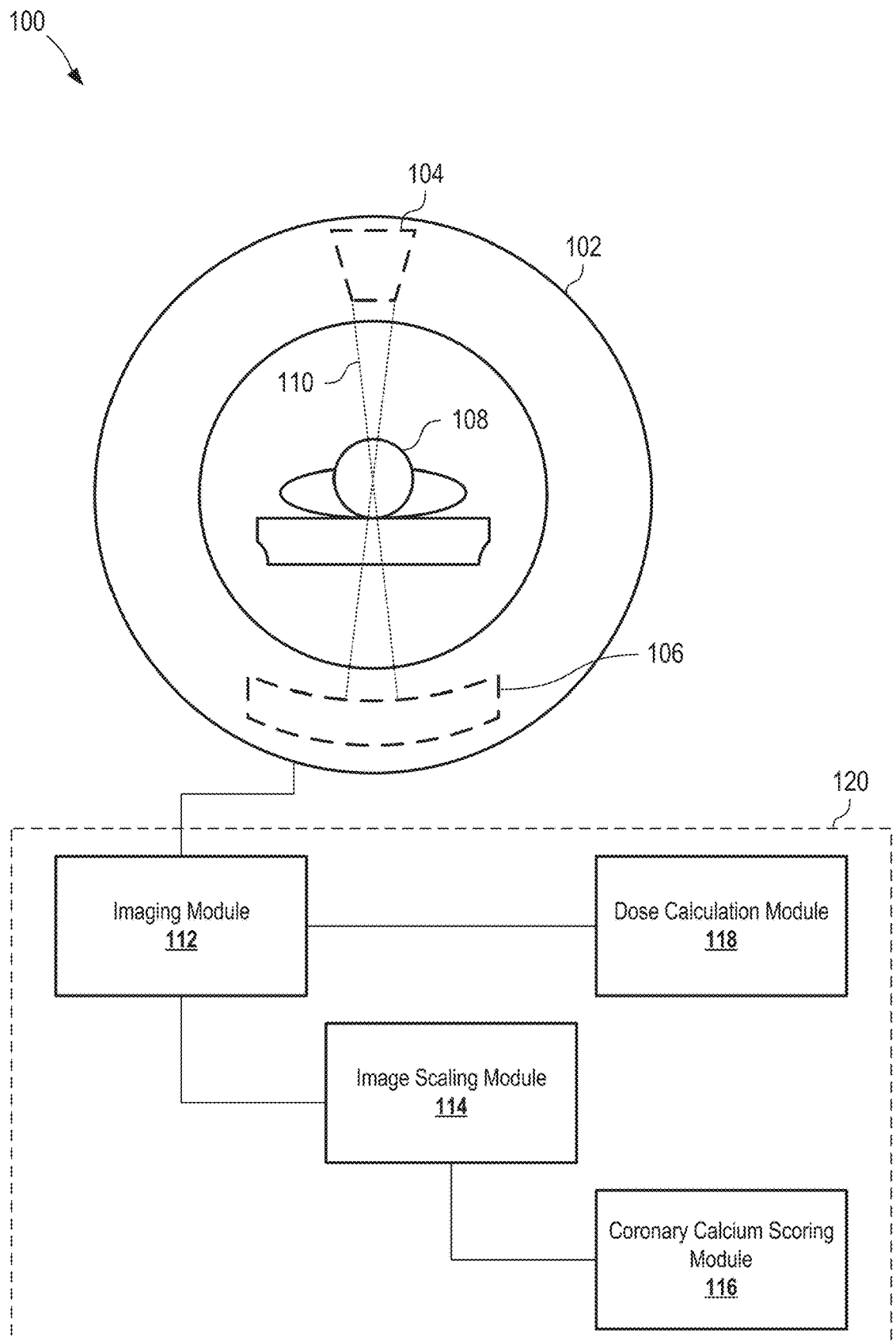
FIG. 1 is a schematic diagram of a system for assessing a coronary calcium score, according to certain aspects of the present disclosure.

Certain aspects and features of the present disclosure relate to determining dose for a coronary calcium scoring (CCS) computed tomography (CT) scan (e.g., a volume CT dose index (CTDI$_{vol}$)) at a lower tube voltages (e.g., a lower peak kilovoltage (kVp)) for a given reference tube voltage. A dose lookup table can be created and used to determine appropriate dosing for CCS while operating at lower kVp based on a reference kVp. This dose lookup table can be created specifically to achieve a consistent contrast-to-noise (CNR) ratio. Additionally, certain aspects and features of the present disclosure also relate to a kVp-dependent scaling method to process images so standard CCS software can be used with standard Houndsfield unit (HU) thresholds. Images captured at non-standard kVp can be processed according to the disclosed scaling method prior to being transferred to CCS software for scoring based on a presumed standard kVp.

In CT scanning, a peak kilovoltage (kVp), also known as a peak tube voltage or a tube voltage, is a measurement of the voltage applied across the x-ray tube to generate x-rays, and more specifically a measurement proportional to the maximum energy of the emitted x-rays. The peak kilovoltage used during a scan defines the amount of radiographic contrast of the resultant image (e.g., the ratio of transmitted radiation through regions of differing density or thickness). Depending on the tissue being imaged, different kVps are needed to provide appropriate contrast to the image. For CCS, a peak tube voltage of 120 kV is used in order to provide suitable contrast for scoring regions of calcification.

In addition to tube voltage, tube current and exposure time can be adjusted, which can be measured in milliamperes (mA) and seconds (s), respectfully, or combined as mA*s. While tube voltage controls the energy of the x-rays that are produced (e.g., and thus their ability to penetrate different densities of tissue), tube current controls the number of x-rays produced for a unit time and exposure time controls the amount of time x-rays are produced to generate the image. Thus, for any given kVp, the overall dose can be adjusted by making changes in tube current and exposure time. However, such changes can affect the subsequent contrast and signal-to-noise ratio of the resultant image.

Existing CCS technologies and scoring methodologies rely on the assumption of a CT scan with a kVp of 120 kV. Other attempts to use lower kVp acquisitions for CCS have been attempted unsuccessfully, due at least in part to a lack of a systematic approach for prescribing the dose for any given kVp. In such attempts adjustment to the lowest CT number threshold was applied without changing the other thresholds, but was unsuccessful in obtaining suitable CCS. While it may be possible to adjust the various thresholds for the different Hounsfield unit ranges in order to make use of lower kVp acquisitions, doing so renders the images unable to be processed using existing and standard CCS software.

Using the current techniques, reducing dose by lowering kVp causes changes in the radiographic contrast of the resultant CT images, which can reduce the signal-to-noise ration and can result in false calcifications appearing in the acquired image. Additionally, changes to the kVp can affect the scores that are generated from standard HU thresholds, requiring ad-hoc adjustments to the HU thresholds to achieve the expected scores. Not only are such adjustments to thresholds for various Hounsfield unit ranges not available using standard CCS software, but such changes may be difficult to ascertain on the fly for each CT scan.

As disclosed herein, appropriate doses for lower kVp acquisitions can be obtained for a given benchmark kVp. Through non-trivial trial and experimentation, it has been determined that the contrast-to-noise ratio for a given sample of calcium exhibits a power relationship with the dose ($CTDI_{vol}$) and with kVp. Leveraging this power relationship, an appropriate dose can be calculated for a desired kVp in which the calcium being imaged will exhibit the same contrast-to-noise ratio (CNR) as that of a reference kVp.

In some cases, this relationship between CNR and $CTDI_{vol}$ and kVp can be used to generate a dose lookup table for various kVp settings. To maintain the same CNR of calcium as a scan with a kVp of 120 kV, the corresponding $CTDI_{vol}$ may need to be reduced by a certain factor, depending on the kVp used. For example, in order to maintain the same CNR of calcium as a scan with a kVp of 120 kV, the corresponding $CTDI_{vol}$ may need to be reduced by a factor of 0.80 for a scan with a kVp of 100, a factor of 0.70 for a scan with a kVp of 90, a factor of 0.60 for a scan with a kVp of 80, and a factor of 0.51 for a scan with a kVp of 70. In an example case, for an individual with an average chest size, such as an anterior-posterior (AP) chest size of at or approximately 22 cm and a lateral (LAT) chest size of at or approximately 32 cm, the aforementioned factors were especially useful. In another example case, for an individual with a larger chest size, such as one with an AP chest size of at or approximately 33 cm and a LAT chest size of at or approximately 43 cm, the following factors can be especially useful: a factor of 0.80 for a scan with a kVp of 100, a factor of 0.70 for a scan with a kVp of 90, a factor of 0.61 for a scan with a kVp of 80, and a factor of 0.51 for a scan with a kVp of 70. In another example case, the following factors were found to be especially useful: a factor of 0.80 for a scan with a kVp of 100, a factor of 0.70 for a scan with a kVp of 90, a factor of 0.60 for a scan with a kVp of 80, and a factor of 0.51 for a scan with a kVp of 70.

When acquiring CT images using lower-than-standard kVps, the calcium HU scores will be intrinsically enhanced. While the dose can be adjusted, such as disclosed herein, to maintain a desired CNR, doing so may alter the HU thresholds necessary to achieve the appropriate CAC score (e.g., as determined form a standard dose, standard kVp scan). However, instead of adjusting the HU thresholds used to calculate the CAC score, the present disclosure provides a technique for pre-processing the CT images so that they can be scored using the standard HU thresholds, and thus can be scored using standard CCS software.

As disclosed herein, CT images acquired at kVps lower than a reference kVp and with reduced dose can be pre-processed to achieve a desired CNR, which can be analyzed using standard CCS software. The pre-processing can involve scaling each pixel in an acquired image. Specifically, each pixel can be scaled by the factor that enhanced the calcium due to the lower kVp, which is a kVp-dependent factor. For example, at a kVp of 70 kV, the factor is at or approximately 1.59; at a kVp of 80 kV, the factor is at or approximately 1.38; at a kVp of 90 kV, the factor is at or approximately 1.24; and at a kVp of 100 kV, the factor is at or approximately 1.14. After applying this preprocessing to the CT images, they can be analyzed using the standard CCS software using the standard HU thresholds.

In some cases, the $CTDI_{vol}$ at the reference kVp of 120 for a given subject can be calculated based on that subject's size (e.g., chest size, such as chest diameter or effective chest diameter). Through non-trivial trial and experimentation, it has been determined that a suitable formula for calculating $CTDI_{vol}$ at a given subject's size can be based on experimental data acquired from two known sample sizes (e.g., a sample subject greater than the given subject's chest size and a sample subject smaller than the given subject's size). In such cases, an appropriate $CTDI_{vol}$ for a subject can be calculated even more precisely based on that subject's specific anatomy (e.g., chest size).

Various aspects and features of the present disclosure can be implemented in various ways, including as a standalone system, a standalone module, a system combined with a CCS software system (e.g., a separate program running on the same computing device as the CCS software), a system combined with a CT imager, a module of a CCS software system or CT imaging system (e.g., a plug-in), or the like.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram of a system 100 for assessing a coronary calcium score, according to certain aspects of the present disclosure. The system 100 can include a scanner 102 (e.g., CT scanner) into which a patient 108 can be placed for image acquisition. The scanner 102 can include a radiation source 104 (e.g., an x-ray tube) and a detector 106 (e.g., a single detector or an array of detectors). The radiation source 104 can cause radiation 110 (e.g., x-rays) to be directed through the patient 108 towards the detector 106 to generate an image. While depicted as a torus-shaped CT scanner in FIG. 1, scanner 102 can be any suitable scanner or scanner configuration.

The scanner 102 can be communicatively coupled to a control and analysis system 120. In some cases, the control and analysis system 120 can be incorporated into a single housing or single computing device, although that need not always be the case. In some cases, various modules of the control and analysis system 120 can be incorporated into multiple computing devices, such as a first computing device for obtaining CT scans (e.g., a control system) and a second computing device for analyzing the CT scans (e.g., an analysis system). In such an example, the control system may include the imaging module 112, the dose calculation module 118, and the image scaling module 114, while the analysis system may include the coronary calcium scoring module 116. In some cases, other arrangements of modules may be used.

The scanner 102 can be controlled by the imaging module 112 to obtain scanner data (e.g., images). The scanner data can include pixel-based and/or volumetric data associated with the type of scan being performed, and can be presented as a set of images and/or image slices. In a CT scanner, the scanner data can be one or more CT images, which can be stored as one or more CT scan files. The imaging module 112 can control various factors of the scanning process, such as the peak tube voltage (kVp), tube current (mA), and exposure time (s).

The imaging module 112 can be communicatively coupled to a dose calculation module 118, which can assist in calculating a needed dose for a given kVp. While standard CCS CT scans may operate at a kVp of 120 kV, system 100 can be used with kVps below 120 kV, such as at or approximately 100 kV, 90 kV, 80 kV, and/or 70 kV, although other kVps below 120 kV may be used. When a non-standard kVp (e.g., not 120 kV) is desired, such as to reduce the overall dose of radiation to the patient 108, the dose calculation module 118 can determine an appropriate dose, and thus appropriate tube current-time product (mA*s), at which the scanner 102 must be driven for the given target kVp to achieve accurate CCS results.

In some cases, dose calculation module 118 can include memory containing a lookup table. In such cases, dose calculation module 118 can apply the target kVp to the lookup table to determine the appropriate dose. In some cases, dose calculation module 118 can include a memory containing a formula. In such cases, dose calculation module 118 can apply the target kVp to the formula to determine the appropriate dose.

The imaging module 112 can use the appropriate dose determined by the dose calculation module 118 to drive the scanner 102. At a given target kVp, the appropriate dose can be used to calculate the necessary tube current-time product (mA*s) for the scan. The imaging module 112 can then use the calculated parameters (e.g., mA and s) to drive the radiation source 104 of the scanner 102 at the desired target kVp for the appropriate amount of time and at the appropriate current based on the calculated parameters. As a result, the detector 106 will generate signal data in the form of scanner data (e.g., CT image(s)).

After obtaining the scanner data, the imaging scaling module 114 can perform pre-processing to the scanner data dependent upon the target kVp used. The imaging module 112 can send the scanner data and the target kVp used to the image scaling module 114, which can scale each pixel of the image (or voxel of the volumetric image) by a reduction factor. The reduction factor can be a kVp-dependent reduction factor.

In some cases, image scaling module 114 can include memory containing a lookup table. In such cases, image scaling module 114 can apply the target kVp to the lookup table to determine the appropriate reduction factor. In some cases, image scaling module 114 can include a memory containing a formula. In such cases, image scaling module 114 can apply the target kVp to the formula to determine the appropriate reduction factor.

After the scanner data has been scaled by the image scaling module 114, this pre-processed scanner data can be analyzed using the coronary calcium scoring module 116. The coronary calcium scoring module 116 can be standard CCS software used to analyze CT scan data to generate an Agatston score. The coronary calcium scoring module 116 can analyze the incoming data (e.g., the pre-processed scanner data) based on traditional Hounsfield unit thresholds to generate the Agatston score, such as using traditional techniques. The system can output the Agatston score, such as on a display. In some cases, the display can annotate or highlight regions of the scanned data (e.g., image) based on the Hounsfield unit scores.

In some cases, all elements of the system 100 can be located in a single environment or facility, however that need not be the case. In some cases, some elements can be located in other locations and/or used non-sequentially. For example, in some cases, a radiologist or cardiologist may analyze the scanner data (e.g., analyze the post-processed scanner data or post-process and then analyze the scanner data) in a separate location from the scanner 102 and/or at a very different time than when the scan was completed (e.g., several days later).

In some cases, various functions of the various modules of the control and analysis system 120 can be automatic, without requiring additional user input. For example, after setting a target kVp, the dose calculation module 118 may automatically determine the appropriate dose and dose parameters (e.g., mA and s) and feed those to the imaging module 112. In another example, after performing the scan, the image scaling module 114 may automatically pre-process the scanner data, such as before or immediately after saving the scanner data to a storage medium.

Figure 2:
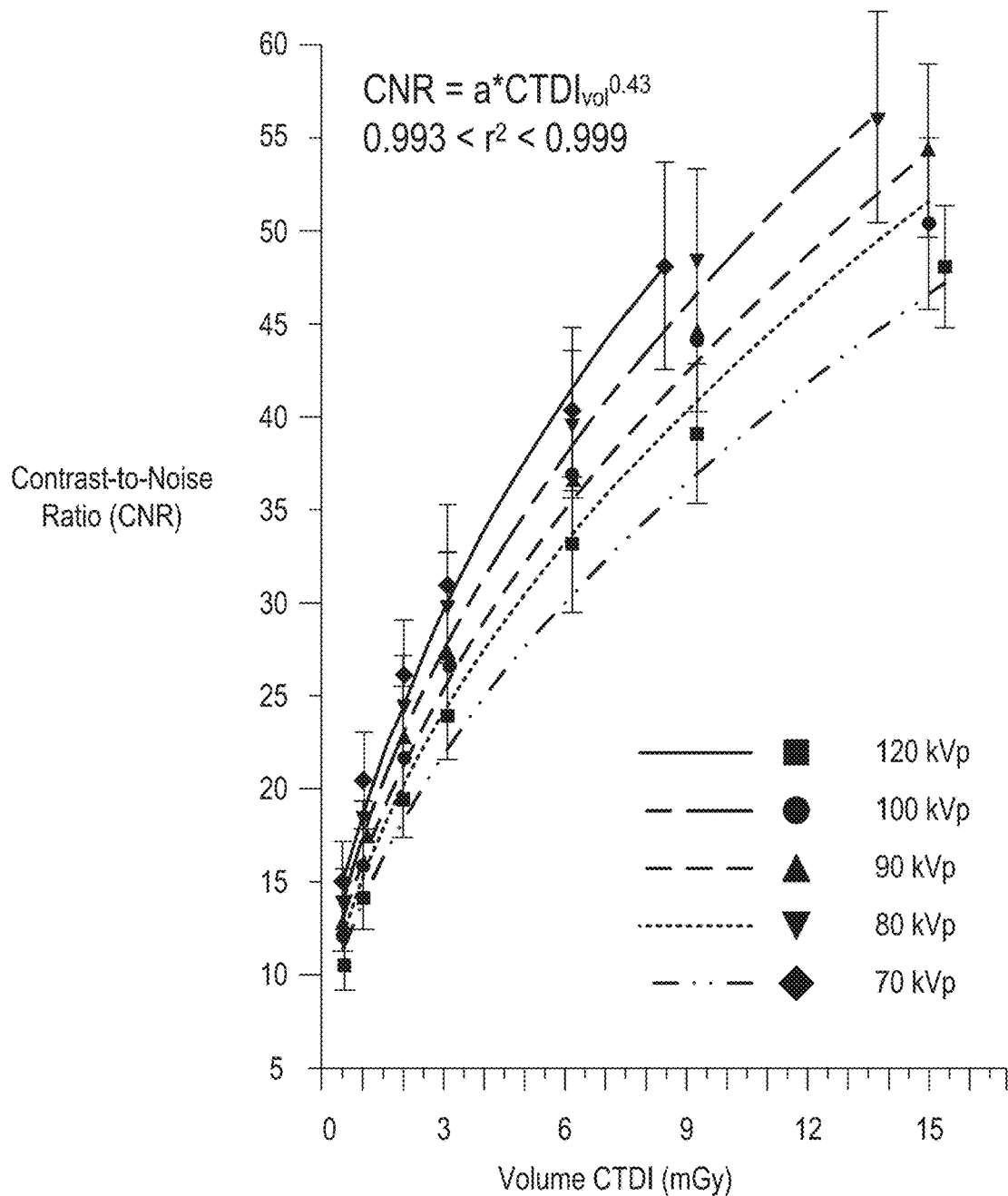
FIG. 2 is a graph depicting contrast-to-noise ratio versus dose for an example 200 mg/cc sample at various kVps, according to certain aspects of the present disclosure.
Figure 3:
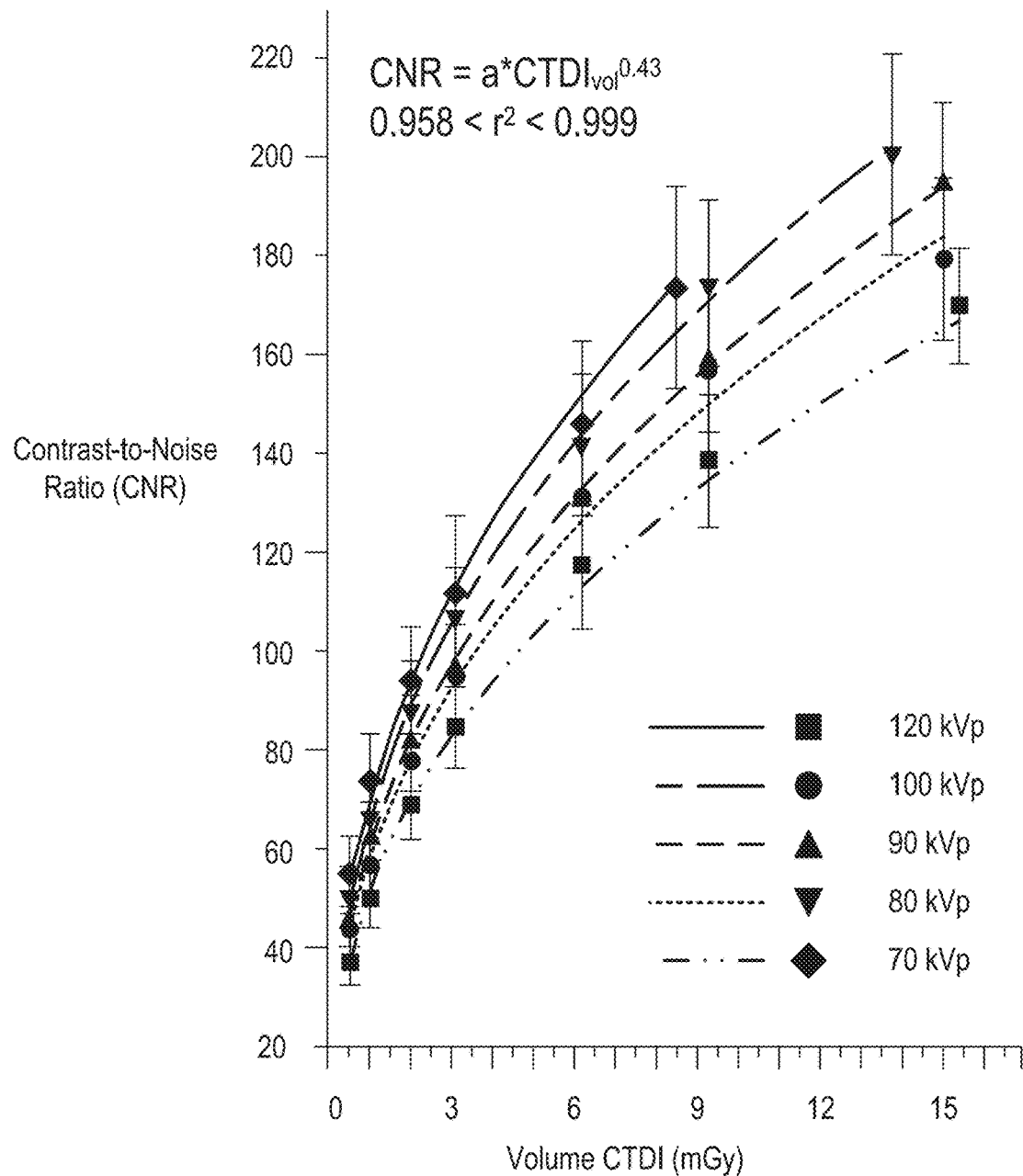
FIG. 3 is a graph depicting contrast-to-noise ratio versus dose for an example 800 mg/cc sample at various kVps, according to certain aspects of the present disclosure.

FIGS. 2-3 are graphs 200, 300 depicting contrast-to-noise ratio versus dose for an example 200 mg/cc sample and an example 800 mg/cc sample, respectfully, at various kVps, according to certain aspects of the present disclosure. Any suitable system can be used to generate the results depicted in graphs 200, 300, such as system 100 of FIG. 1.

The contrast-to-noise ratio of a radiographic image (e.g., scanner data) is an important metric in differentiating tissues. Since the Agatston score is based on identifying regions of calcification in CT scans, it relies on contrast differences between the calcium in the coronary arteries and the surrounding tissue. As kVp decreases, the contrast-to-signal ratio will change.

To generate the results of graph 200, CT scans were taken using an anthropomorphic heart phantom with inserts of hydroxyapatite (HA) having a density of 200 mg/cc. Soft tissue rods were used to fill the air cavity. The hydroxyapatite inserts accurately mimic calcification in the coronary arteries of the heart phantom. CT scans were taken using dual-source axial mode and manual techniques at various combinations of kVp and $CTDI_{vol}$. CT scans sets were taken at kVps of 120 kV, 100 kV, 90 kV, 80 kV, and 70 kV. For each scan set, scans were taken for various doses ($CTDI_{vol}$) from 0.5 to 15 mGy. Each scan was repeated three times and the images were reconstructed to a typical slice thickness (e.g., 3 mm) without iterative reconstruction. The CNR of the hydroxyapatite inserts was measured among all slices and the mean values were fitted to a function of $CTDI_{vol}$ at each kVp. The results were further fitted to a function of kVp. A residual analysis was performed to demonstrate the fitting accuracy.

The results of graph 300 were generated using the same technique as those of graph 200, except with the use of hydroxyapatite inserts having a density of 800 mg/cc instead of 200 mg/cc.

As depicted in FIGS. 2-3, the relationship between CNR and $CTDI_{vol}$ can be shown according to the equation (1), in which a is a kVp-dependent parameter:

$$CNR = a * CTDI_{vol}^{0.43} \quad (1)$$

The kVp-dependent parameter was fit as described with reference to FIG. 4.

Figure 4:
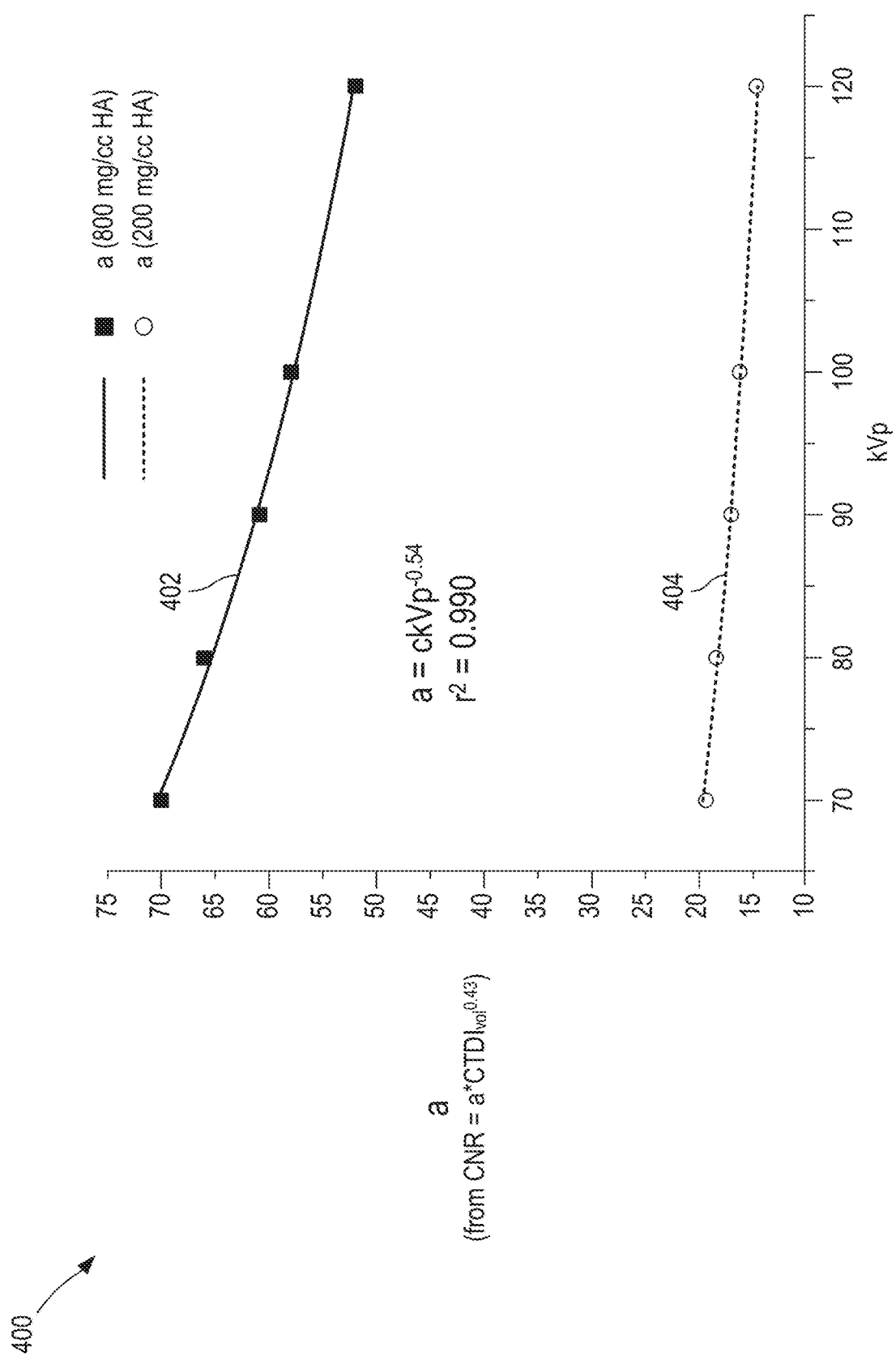
FIG. 4 is a graph depicting the fitting of parameter "a" from the CNR-to-CTDI$_{vol}$ equations of examples of FIGS. 2-3, according to certain aspects of the present disclosure.

FIG. 4 is a graph 400 depicting the fitting for parameter "a" of the CNR-to-$CTDI_{vol}$ equations from the examples of FIGS. 2-3, according to certain aspects of the present disclosure. The fitting for parameter "a" is depicted for the two different hydroxyapatite densities (e.g., 200 mg/cc and 800 mg/cc) from the examples of FIGS. 2-3. Based on the fitting results shown in graph 400, the parameter a can be described by equation (2), where c is a proportionality constant dependent on the calcium physical density:

$$a = ckVp^{-0.54} \quad (2)$$

It was determined that the CNR was fitted to a power relationship with $CTDI_{vol}$ and kVp ($r^2 > 0.958$). As further supported with reference to FIGS. 3-4, the power indices were found to be 0.43 and −0.54, respectively. The average residual was less than 3%. Based on the findings, in order to maintain the same CNR of calcium as at a kVp of 120 kV, the corresponding $CTDI_{vol}$ for kVps of 100 kV, 90 kV, 80 kV, and 70 kV can be reduced by factors of 0.80, 0.70, 0.60, and 0.51, respectively.

Thus, for the 200 and 800 mg/cc samples of hydroxyapatite, the equations relating the CNR to kVp and $CTDI_{vol}$ are as follows:

$$CNR\left(200 \frac{mg}{cc}\right) = c_1 * kVp^{-.54} * CTDI_{vol}^{0.43} \quad (3)$$

$$CNR\left(800 \frac{mg}{cc}\right) = c_2 * kVp^{-.54} * CTDI_{vol}^{0.43} \quad (4)$$

To accommodate for different densities, the appropriate dose for a particular kVp can be based on the appropriate dose for a reference kVp, such as the standard kVp of 120 kV used for traditional CCS. Therefore, to achieve the same CNR as achieved with a reference kVp, an appropriate dose for a particular target kVp below a reference kVp can be obtained using equation (5), where $CTDI_{vol}$ and $CTDI_{vol,ref}$ are measured in mGy and kVp is measured in kV:

$$CTDI_{vol} = \left(\frac{kVp_{target}}{kVp_{ref}}\right)^{1.246} * CTDI_{vol,ref} \quad (5)$$

Applied to a reference kVp of 120 kV, equation (5) becomes:

$$CTDI_{vol} = \left(\frac{kVp_{target}}{120}\right)^{1.246} * CTDI_{vol,ref} \quad (6)$$

Figure 5:
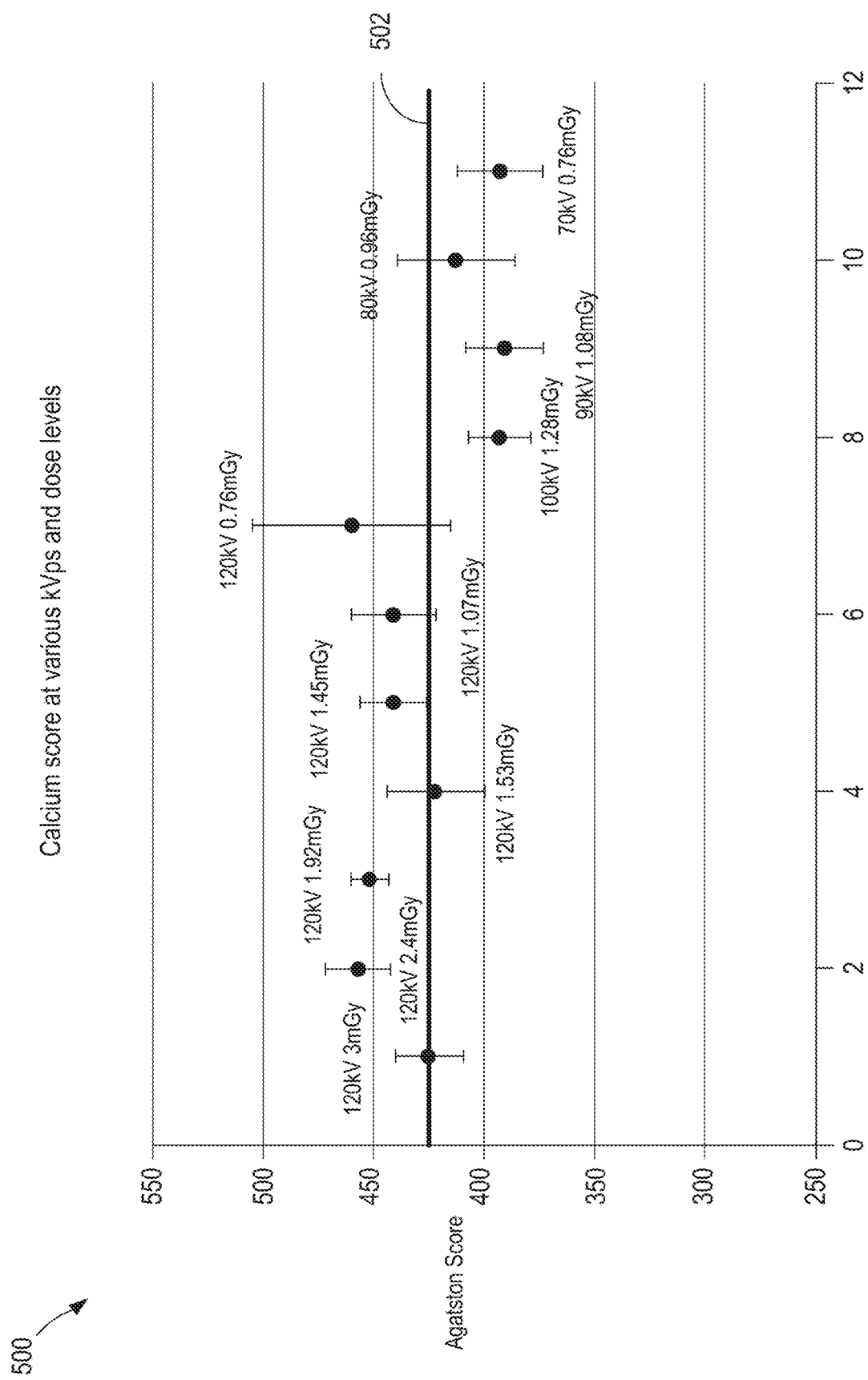
FIG. 5 is a graph depicting the Agatston score for an example sample at various kVps and dose, according to certain aspects of the present disclosure.

FIG. 5 is a graph 500 depicting the Agatston score for an example sample at various kVps and dose, according to certain aspects of the present disclosure. The data represented in graph 500 is for a sample that is a medium size phantom. Standard techniques CCS rely on acquisitions with a kVp of 120 kV, which limit dose reduction to mA adjustment. The utilization of lower kVp makes further dose reduction possible, but the intrinsic calcium enhancement at each kVp would normally require multiple HU threshold adjustments for scoring.

As depicted in FIG. 5, Agatston scores are calculated across different combinations of $CTDI_{vol}$ and kVps, as labelled above or below each measurement on the graph 500. For illustrative purposes, the y-axis of graph 500 depicts the Agatston score and the x-axis depicts cases of various doses and kVps. The Agatston score taken at 3 mGy and 120 kV is used to define the horizontal reference line at an Agatston score of approximately 425.

To obtain the results depicted in graph 500, Hydroxyapatite inserts of different densities (e.g., 50, 100, 250 and 400 mg/cc) and different sizes (e.g., 1.2-5 mm) were placed inside a dynamic heart phantom within the coronary segments to simulate coronary calcium. The phantom was set in 3D motion with an ECG of 60 beats-per-minute and was scanned on a CT using a kVp of 120 kV and at various doses (e.g., $CTDI_{vol}$ 0.76-3 mGy). Scans were taken at lower kVps (e.g., at 100, 90, 80 and 70), in which cases each scan dose was set to achieve a consistent contrast-to-noise ratio (CNR) as that of the clinical technique for the phantom size (e.g., 120 kVp and 1.56 mGy). Each scan was repeated six times and the images were reconstructed to 3 mm without iterative reconstruction.

The pixel values of the lower kVp images were scaled down by the previously found calcium CT number enhancement ratio relative to 120 kVp. This processing maintained the calcium CNR and the Agatston score thresholds (e.g., HU thresholds). Standard CCS software was used to obtain the coronary calcium scores for all image sets by six independent readers.

Line 502 represents the reference score, which is based on the reference images from the 120 kVp acquisition at the $CTDI_{vol}$ of 3.0 mGy. As depicted in graph 500, after the aforementioned correction (e.g., pre-processing), the final Agatston scores of the acquisitions at various kVp below 120 kV are nevertheless accurate when compared to the reference score.

It was determined that in order to maintain the same HU thresholds for calcium as at a kVp of 120 kV, the pixels of images acquisitions taken at kVps of 100 kV, 90 kV, 80 kV, and 70 kV can be scaled down by factors of 1.14, 1.24, 1.38, and 1.59, respectively.

Figure 6A:
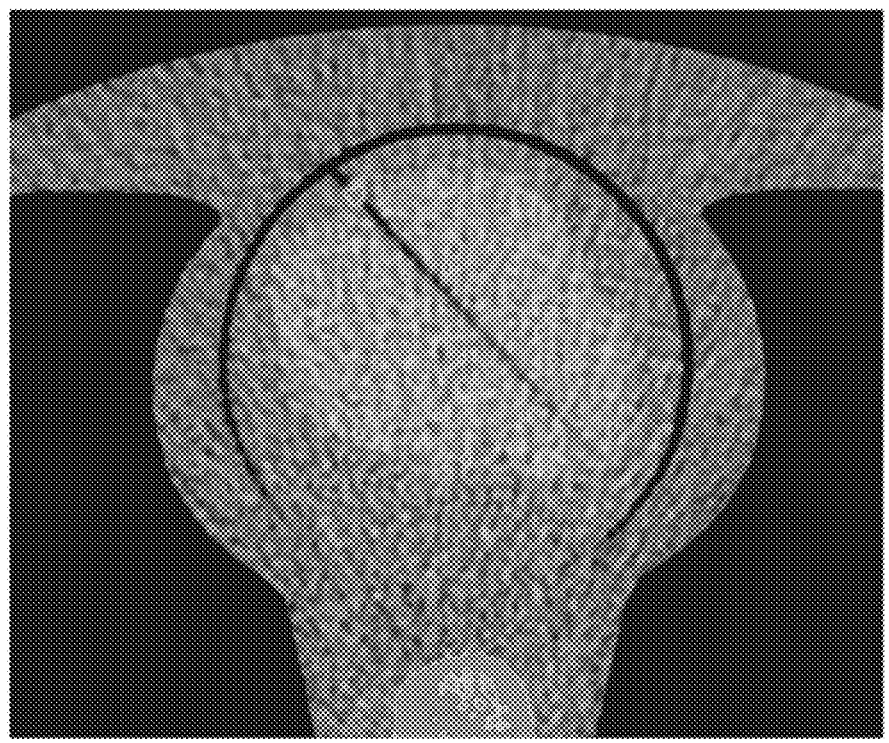
FIG. 6A is a CT image of an example sample showing significant false calcifications, according to certain aspects of the present disclosure.

FIG. 6A is a CT image 600 of an example sample showing significant false calcifications, according to certain aspects of the present disclosure. Image 600 was acquired at a kVp of 120 kV and a $CTDI_{vol}$ of 0.76 mGy. Image 600 shows significant false calcifications.

Figure 6B:
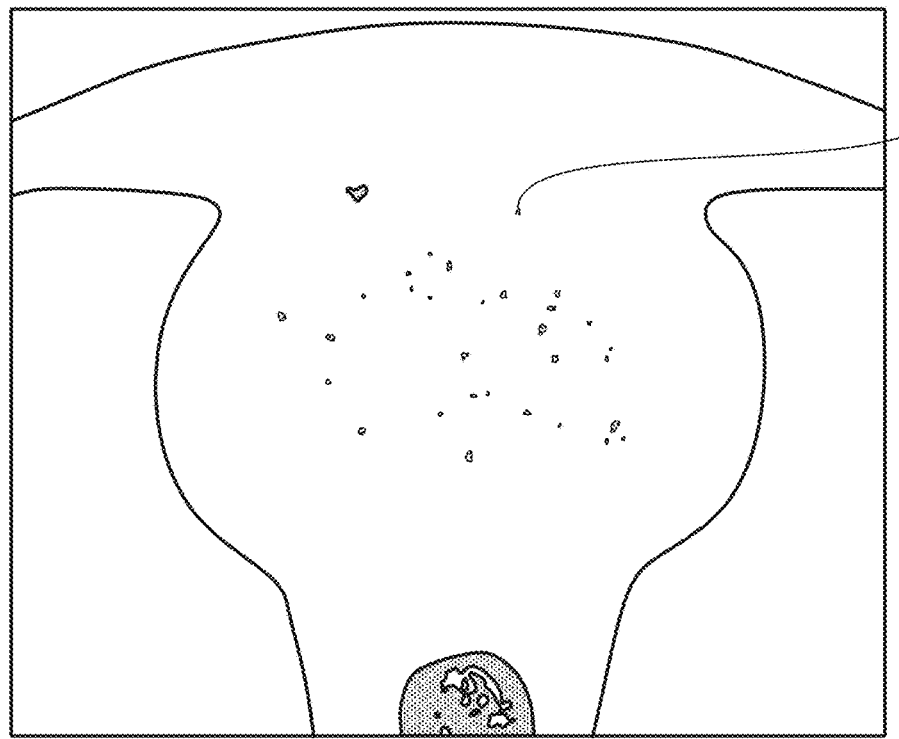
FIG. 6B is a simplified graphic representation of the CT image of FIG. 6A, according to certain aspects of the present disclosure.

FIG. 6B is a simplified graphic representation 601 of the CT image 600 of FIG. 6A, according to certain aspects of the present disclosure. For illustrative purposes, the simplified graphic representation 601 shows only the outline of the sample along with indications 602 of calcium deposits. Thus, the regions identified as calcium deposits from image 600, including all of the false calcifications (e.g., most of the small annotated speckles), are depicted as indications 602 in the simplified graphic representation 601.

Figure 7A:
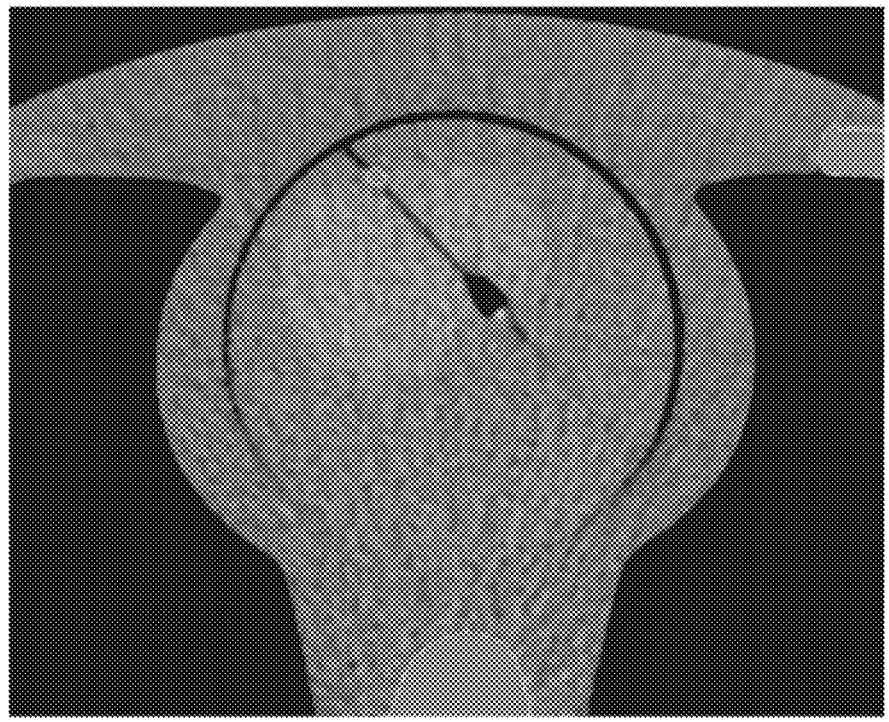
FIG. 7A is a CT image of the example sample of FIG. 6A, showing minimized false calcifications, according to certain aspects of the present disclosure.

FIG. 7A is a CT image 700 of the example sample showing minimized false calcifications, according to certain aspects of the present disclosure. The CT image 700 was acquired at a kVp of 70 kV and the same $CTDI_{vol}$ of 0.76 mGv. As depicted in FIG. 7A, the image 700 shows minimized false calcifications when compared to image 600 of FIG. 6A.

Figure 7B:
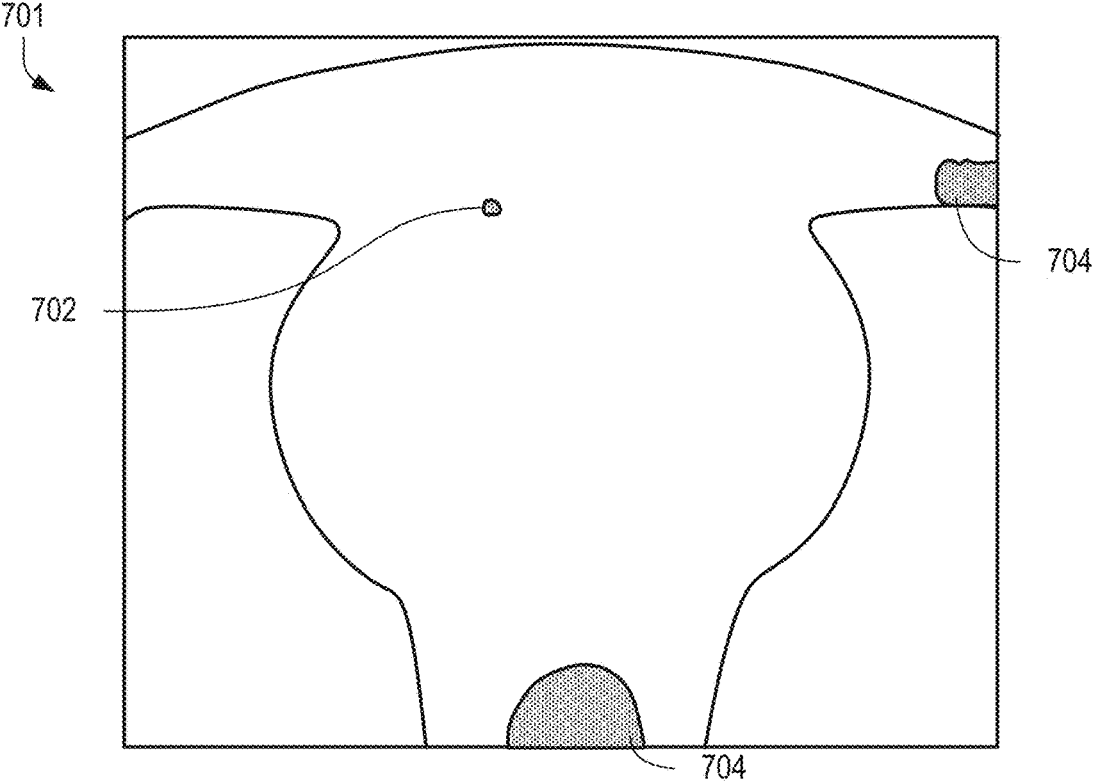
FIG. 7B is a simplified graphic representation of the CT image of FIG. 7A, according to certain aspects of the present disclosure.

FIG. 7B is a simplified graphic representation 701 of the CT image 700 of FIG. 7A, according to certain aspects of the present disclosure. For illustrative purposes, the simplified graphic representation 701 shows the outline of the sample along with indication 702 of calcium deposits. Thus, the regions identified as calcium deposits from image 700 are depicted as indication 702 in the simplified graphic representation 701. Areas 704 are regions of bone.

Figure 8:
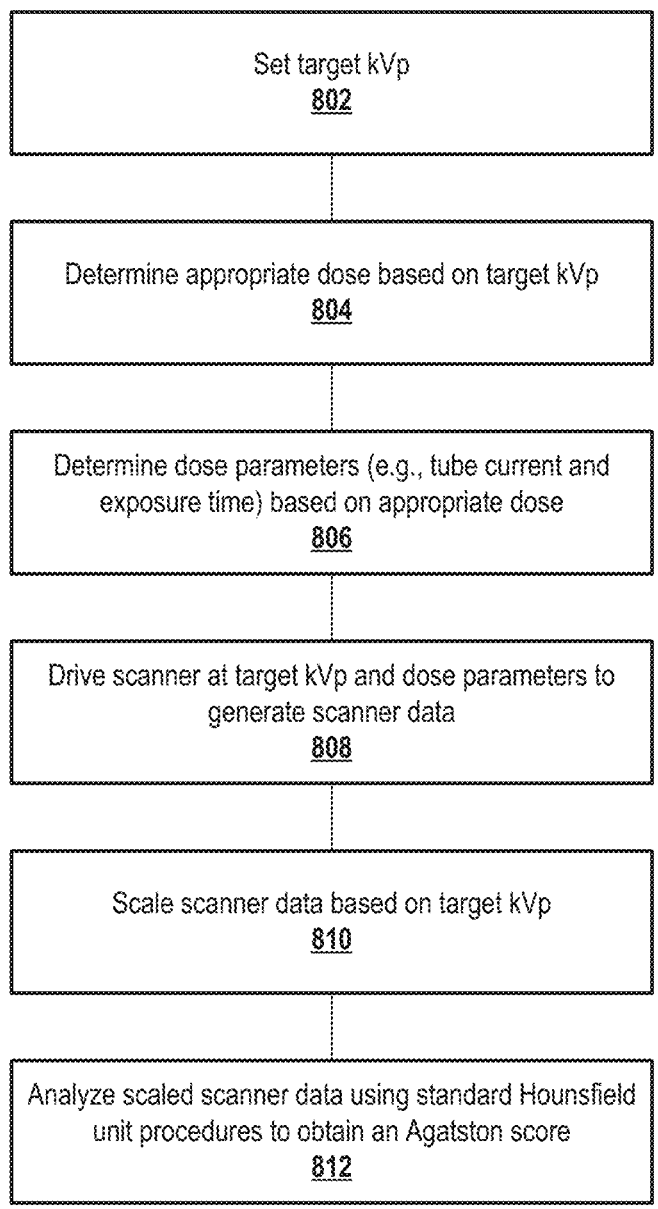
FIG. 8 is a flowchart depicting a process for obtaining a coronary calcium score, according to certain aspects of the present disclosure.

FIG. 8 is a flowchart depicting a process 800 for obtaining a coronary calcium score, according to certain aspects of the present disclosure. Process 800 can be performed by system 100 of FIG. 1, or any other suitable system.

At block 802, a target kVp can be set. The target kVp can be selected from a list of available kVp or can be otherwise selected. As used herein, determining a target kVp can include automatically determining a target kVp or manually determining a target kVp (e.g., based on user input or selection of a target kVp). At block 804, the target kVp can be used to determine an appropriate dose (e.g., $CTDI_{vol}$). Determining the appropriate dose can make use of any of the equations as described above with reference to FIGS. 2-4. In some cases, determining the appropriate dose based on the target kVp includes applying equation (7):

$$CTDI_{vol} = \left(\frac{kVp_{target}}{kVp_{ref}}\right)^{1.246} * CTDI_{vol,ref} \qquad (7)$$

In some cases, determining the appropriate dose can include accessing a lookup table and applying the target kVp to the lookup table to identify an appropriate dose.

In some cases, the reference dose (e.g., dose at the reference kVp, or $CTDI_{vol,ref}$) can itself be determined or modified based on the size of the patient (e.g., the diameter of the patient's chest), such as described with reference to FIGS. 13-14.

In some cases, instead of setting a target kVp at block 802 and then determining an appropriate dose at block 804, the process can be reversed and a target dose can be set first, from which an appropriate kVp can be determined. Other blocks of process 800 can be adjusted accordingly.

At block 806, dose parameters can be determined based on the appropriate dose determined at block 804. Determining dose parameters can include determining an appropriate tube current and exposure time for driving the scanner. Determining dose parameters can include using the target kVp and the $CTDI_{vol}$ from blocks 802 and 804, respectively. In some cases, determining dose parameters can include determining a tube current-time product associated with the target kVp and $CTDI_{vol}$ from blocks 802 and 804. Since the tube current-time product is directly proportional to the $CTDI_{vol}$ determined at block 804 (e.g., proportional based on kVp), appropriate dose parameters can be determined from the $CTDI_{vol}$ using any suitable technique, such as calculating from a formula, measuring on a chart, or applying a lookup table.

At block 808, the scanner can be driven at the target kVp using the dose parameters form block 806. Driving the scanner can include applying voltage through a radiation source, such as an x-ray tube, to achieve a kVp of the target kVp set at block 802 at a current and for an exposure time as dictated by the dose parameters determined at block 806. Applying the appropriate power to the radiation source can energize the radiation source to generate radiation that passes through a target area (e.g., a portion of a patient) towards a detector. Driving the scanner at block 808 can include receiving radiation at the detector and generating scanner data based on the detected radiation. The scanner data can be one or more x-ray images.

At block 810, the scanner data can be scaled based on the target kVp. Scaling the scanner data at block 810 can occur within the scanner (e.g., scanner 102 of FIG. 1), within a control unit for the scanner, or within any other suitable computing device. For example, a scanner system (e.g., scanner and/or control unit for the scanner) can output an already pre-processed (e.g., scaled) image by scaling the scanner data prior to outputting it. Thus, the output from the scanner system can be directly analyzed by a CCS module (e.g., CCS analysis software). In another example, the scanner system can output the non-scaled scanner data, in which case a separate system (e.g., cloud-based computing device or a computing device for analyzing and generating a CAC score) can scale the scanner data prior to a CCS module analyzing the scaled scanned data.

Scaling the scanner data can include adjusting each pixel (or voxel) of an image based on a scaling factor. The scaling factor can be based on the target kVp. For example, at a kVp of 70 kV, the scaling factor is at or approximately 1.58; at a kVp of 80 kV, the scaling factor is at or approximately 1.38; at a kVp of 90 kV, the scaling factor is at or approximately 1.24; and at a kVp of 100 kV, the scaling factor is at or approximately 1.14. As used with reference to this scaling factor, the term "at or approximately" can include the number or within 10%, 9%, 8%, 7%, 6%, 5%, 4%, 3%, 2%, and/or 1% of the number. In an example case, for an individual with an average chest size, such as an anterior-posterior (AP) chest size of at or approximately 22 cm and a lateral (LAT) chest size of at or approximately 32 cm, the aforementioned scaling factors were especially useful. In another example case, for an individual with a larger chest size, such as one with an AP chest size of at or approximately 33 cm and a LAT chest size of at or approximately 43 cm, the following scaling factors can be especially useful: a scaling factor of at or approximately 1.61 when the peak kilovoltage is 70 kV, a scaling factor of at or approximately 1.38 when the peak kilovoltage is 80 kV, a scaling factor of at or approximately 1.24 when the peak kilovoltage is 90 kV, and a scaling factor of at or approximately 1.13 when the scaling factor is 100 kV. In another example case, the following scaling factors were found to be especially useful: a scaling factor of at or approximately 1.59 when the peak kilovoltage is 70 kV, a scaling factor of at or approximately 1.38 when the peak kilovoltage is 80 kV, a scaling factor of at or approximately 1.24 when the peak kilovoltage is 90 kV, and a scaling factor of at or approximately 1.14 when the scaling factor is 100 kV.

In an example, scaling can be performed by generating a new value for each pixel of an image using the current value of each pixel of the image scaled according to equation (8), where k is the scaling factor:

$$New_{image(i,j)} = \text{Nearest integer of } \left(\frac{\text{Image }(i,j)}{k}\right) \qquad (8)$$

Scaling the scanner data at block 810 can include determining the scaling factor based on the kVp used to generate the scanner data (e.g., the target kVp from block 802). Determining the scaling factor can include using any suitable technique, such as calculating from a formula, measuring on a chart, or applying a lookup table.

At block 812, the scaled scanner data can be analyzed. The scaled scanner data can be analyzed to generate a CAC score, such as an Agatston score. The scaled scanner data can be analyzed using standard HU procedures (e.g., standard HU thresholds) to obtain the Agatston score. Thus, the scaled scanner data is usable in standard CCS software to generate an accurate Agatston score, despite the target kVp at block 902 being below the 120 kV standard kVp.

Figure 9:
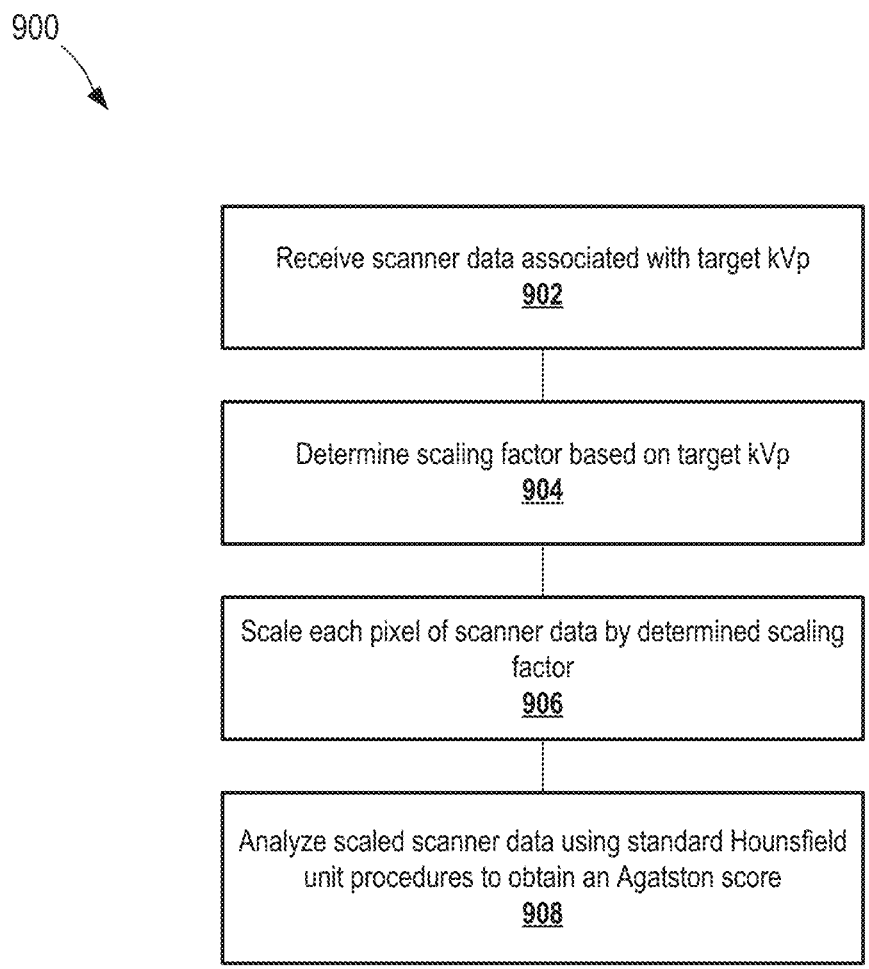
FIG. 9 is a flowchart depicting a process for performing kVp-dependent scaling on a scanner image, according to certain aspects of the present disclosure.

FIG. 9 is a flowchart depicting a process 900 for performing kVp-dependent scaling on a scanner image, according to certain aspects of the present disclosure. In some cases, process 900 can be performed as part of block 810 of process 800 of FIG. 8.

At block 902, scanner data is received. The scanner data can be associated with a target kVp. The target kVp can be other than a standard 120 kV, such as below 120 kV. In some cases, the scanner data includes the kVp, although that need not always be the case. In some cases, the target kVp can be received separately from the scanner data and separately associated with the scanner data.

At block 904, a scaling factor is determined based on the target kVp. Determining the scaling factor can be performed as described with reference to block 810 of FIG. 8. In some cases, determining the scaling factor can include applying the target kVp to a formula, chart, or lookup table designed to produce suitable scaling factors for various target kVps. Such formula, chart, or lookup table can be generated as disclosed herein.

At block 906, each pixel (or voxel) of the scanner data can be scaled according to the scaling factor determined at block 906. Scaling each pixel can include applying the equation described herein with reference to block 810 of FIG. 8.

At block 908, the scaled scanner data can be analyzed. The scaled scanner data can be analyzed to generate a CAC score, such as an Agatston score. The scaled scanner data can be analyzed using standard HU procedures (e.g., standard HU thresholds) to obtain the Agatston score. Thus, the scaled scanner data is usable in standard CCS software to generate an accurate Agatston score, despite the target kVp received at block 902 being below the 120 kV standard kVp.

Figure 10:
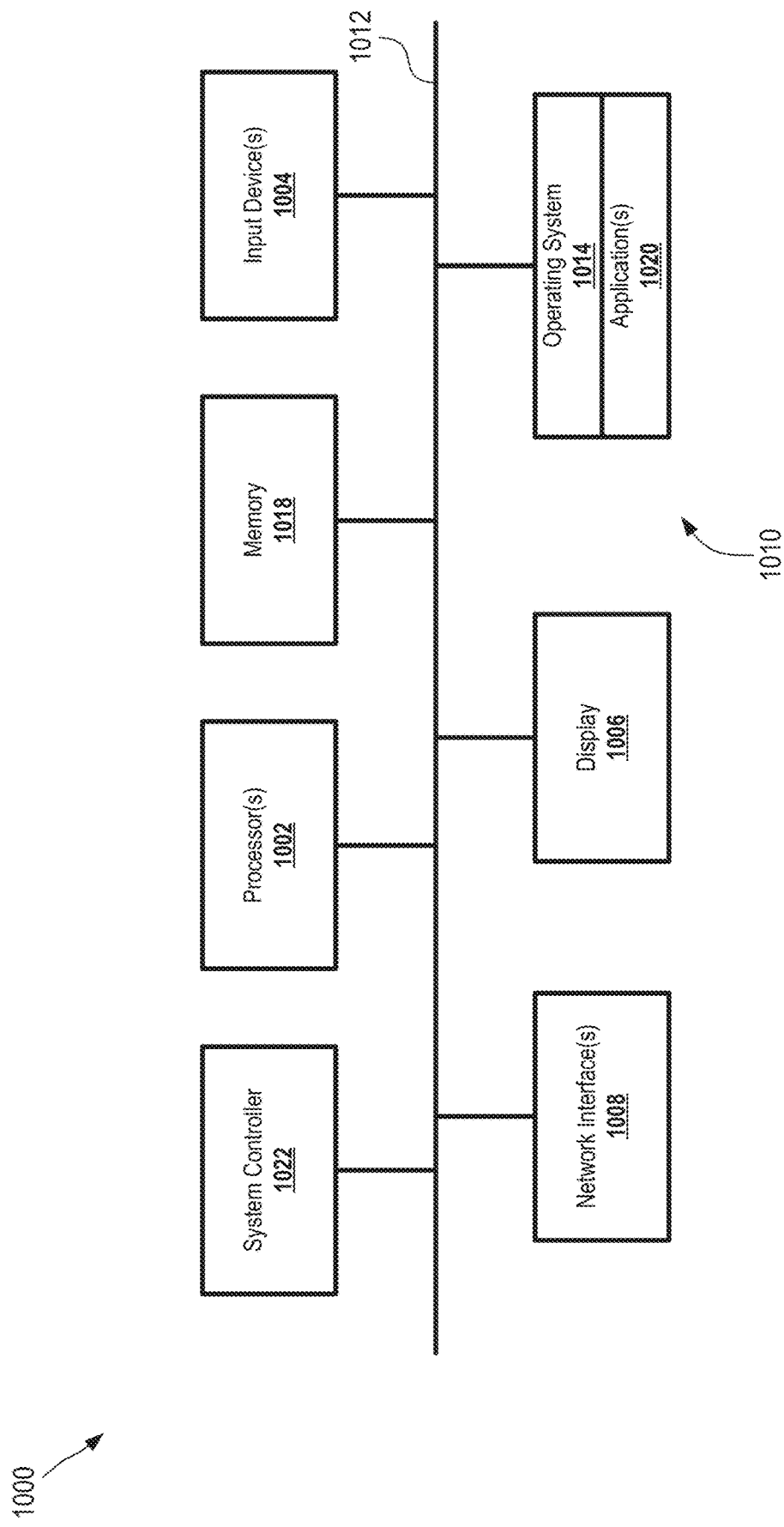
FIG. 10 is a block diagram of an example system architecture for implementing features and processes according to certain aspects of the present disclosure.

FIG. 10 is a block diagram of an example system architecture for implementing features and processes of the present disclosure, such as those presented with reference to FIGS. 1-9. The architecture 1000 can be implemented on any electronic device that runs software applications derived from compiled instructions, including without limitation personal computers, servers, smart phones, electronic tablets, game consoles, email devices, and the like. In some implementations, the architecture 1000 can include one or more processors 1002, one or more input devices 1004, one or more display devices 1006, one or more network interfaces 1008, and one or more computer-readable mediums 1010. Each of these components can be coupled by bus 1012.

In some implementations, system architecture 1000 can correspond to a single server in a rack of servers. Various rack configurations can be implemented. For example, a rack can include multiple chassis and each chassis can contain multiple servers. Each server in the rack can be connected by various hardware components (e.g., backbone, middle plane, etc.). In some implementations, system architecture 1000 can correspond to a control console for a CT scanner and/or multiple devices coupled to a single control console for a CT scanner.

Display device 1006 can be any known display technology, including but not limited to display devices using Liquid Crystal Display (LCD) or Light Emitting Diode (LED) technology. Processor(s) 1002 can use any known processor technology, including but not limited to graphics processors and multi-core processors. Input device 1004 can be any known input device technology, including but not limited to a keyboard (including a virtual keyboard), mouse, track ball, and touch-sensitive pad or display. Bus 1012 can be any known internal or external bus technology, including but not limited to ISA, EISA, PCI, PCI Express, NuBus, USB, Serial ATA or FireWire.

Computer-readable medium 1010 can be any medium that participates in providing instructions to processor(s) 1002 for execution, including without limitation, non-volatile storage media (e.g., optical disks, magnetic disks, flash drives, etc.) or volatile media (e.g., SDRAM, ROM, etc.). The computer-readable medium (e.g., storage devices, mediums, and memories) can include, for example, a cable or wireless signal containing a bit stream and the like. However, when mentioned, non-transitory computer-readable storage media expressly exclude media such as energy, carrier signals, electromagnetic waves, and signals per se.

Computer-readable medium 1010 can include various instructions for implementing operating system 1014 and applications 1020 such as computer programs. The operating system can be multi-user, multiprocessing, multitasking, multithreading, real-time and the like. The operating system 1014 performs basic tasks, including but not limited to: recognizing input from input device 1004; sending output to display device 1006; keeping track of files and directories on computer-readable medium 1010; controlling peripheral devices (e.g., disk drives, printers, etc.) which can be controlled directly or through an I/O controller; and managing traffic on bus 1012. Computer-readable medium 1010 can include various instructions for implementing firmware processes, such as a BIOS. Computer-readable medium 1010 can include various instructions for implementing any of processes described herein, such as processes 800, 900, 1600 of FIGS. 8, 9, and 16, respectively.

Memory 1018 can include high-speed random access memory and/or non-volatile memory, such as one or more magnetic disk storage devices, one or more optical storage devices, and/or flash memory (e.g., NAND, NOR). The memory 1018 (e.g., computer-readable storage devices, mediums, and memories) can include a cable or wireless signal containing a bit stream and the like. However, when mentioned, non-transitory computer-readable storage media expressly exclude media such as energy, carrier signals, electromagnetic waves, and signals per se. The memory 1018 can store an operating system, such as Darwin, RTXC, LINUX, UNIX, OS X, WINDOWS, or an embedded operating system such as VxWorks.

System controller 1022 can be a service processor that operates independently of processor 1002. In some implementations, system controller 1022 can be a baseboard management controller (BMC). For example, a BMC is a specialized service processor that monitors the physical state of a computer, network server, or other hardware device using sensors and communicating with the system administrator through an independent connection. The BMC is configured on the motherboard or main circuit board of the device to be monitored. The sensors of a BMC can measure internal physical variables such as temperature, humidity, power-supply voltage, fan speeds, communications parameters and operating system (OS) functions.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java), including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computing system that includes a back-end component, such as a data server, or that includes a middleware component, such as an application server or an Internet server, or that includes a front-end component, such as a client computer having a graphical user interface or an Internet browser, or any combination thereof. The components of the system can be connected by any form or medium of digital data communication such as a communication network. Examples of communication networks include, e.g., a LAN, a WAN, and the computers and networks forming the Internet.

The computing system can include clients and servers. A client and server are generally remote from each other and typically interact through a network. The relationship of client and server arises by virtue of computer programs running on the respective computers and having a client-server relationship to each other.

One or more features or steps of the disclosed embodiments can be implemented using an application programming interface (API). An API can define one or more parameters that are passed between a calling application and other software code (e.g., an operating system, library routine, function) that provides a service, that provides data, or that performs an operation or a computation.

The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer will employ to access functions supporting the API.

In some implementations, an API call can report to an application the capabilities of a device running the application, such as input capability, output capability, processing capability, power capability, communications capability, and the like.

Figure 11:
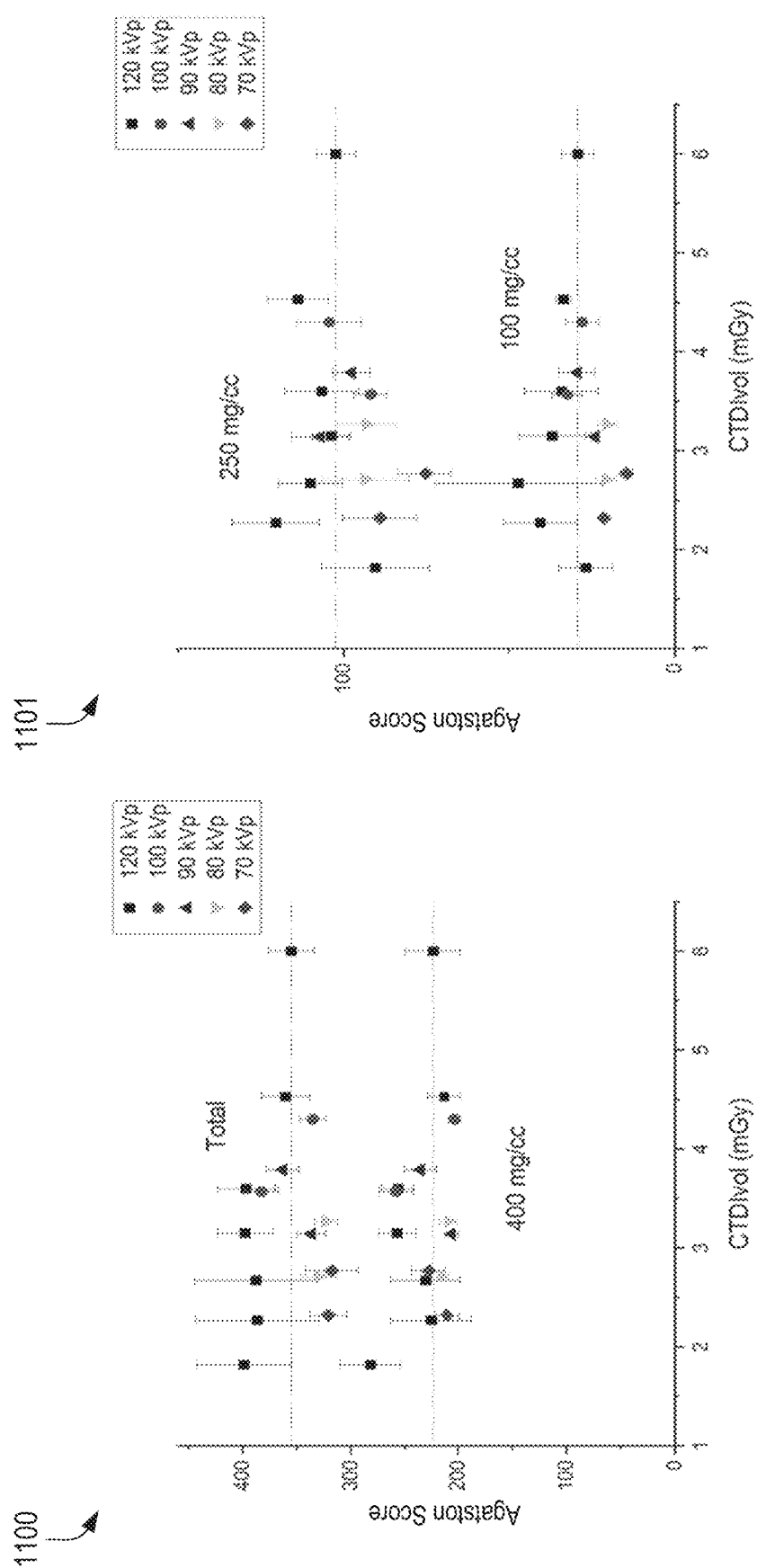
FIG. 11 is a set of charts depicting calcium scores and CTDI$_{vol}$ for scans at various kVp for a large-sized sample, broken out by density of calcification, according to certain aspects of the present disclosure.

FIG. 11 is a set of charts 1100, 1101 depicting calcium scores and $CTDI_{vol}$ for scans at various kVp for a large-sized sample, broken out by density of calcification, according to certain aspects of the present disclosure. The sample used for charts 1100, 1101 can be a large-sized phantom. Charts 1100, 1101 are examples from scanning an example sample equating to an individual having an AP chest size of 33 cm and a LAT chest size of 43 cm.

Charts 1100, 1101 each depict several example scans performed at 120 kVp, 100 kVp, 90 kVp, 80 kVp, and 70 kVp. Chart 1101 depicts the regional calcium scores for calcification densities of 100 mg/cc and 250 mg/cc, whereas chart 1100 depicts the regional calcium score for a calcification density of 400 mg/cc and a total calcium score. For each density level, the dotted line represents the ground truth pinned to the 120 kVp scan at 6 mGy $CTDI_{vol}$.

As seen in charts 1100, 1101, many data points were taken for scans at kVp lower than 120 kVp, with dosages substantially lower than 6 mGy, while achieving the same or similar (e.g., within 10%) calcium scores as the ground truth. Further, the accuracy of the lower tube potential scans appear to even improve with higher-density calcifications.

Figure 12:
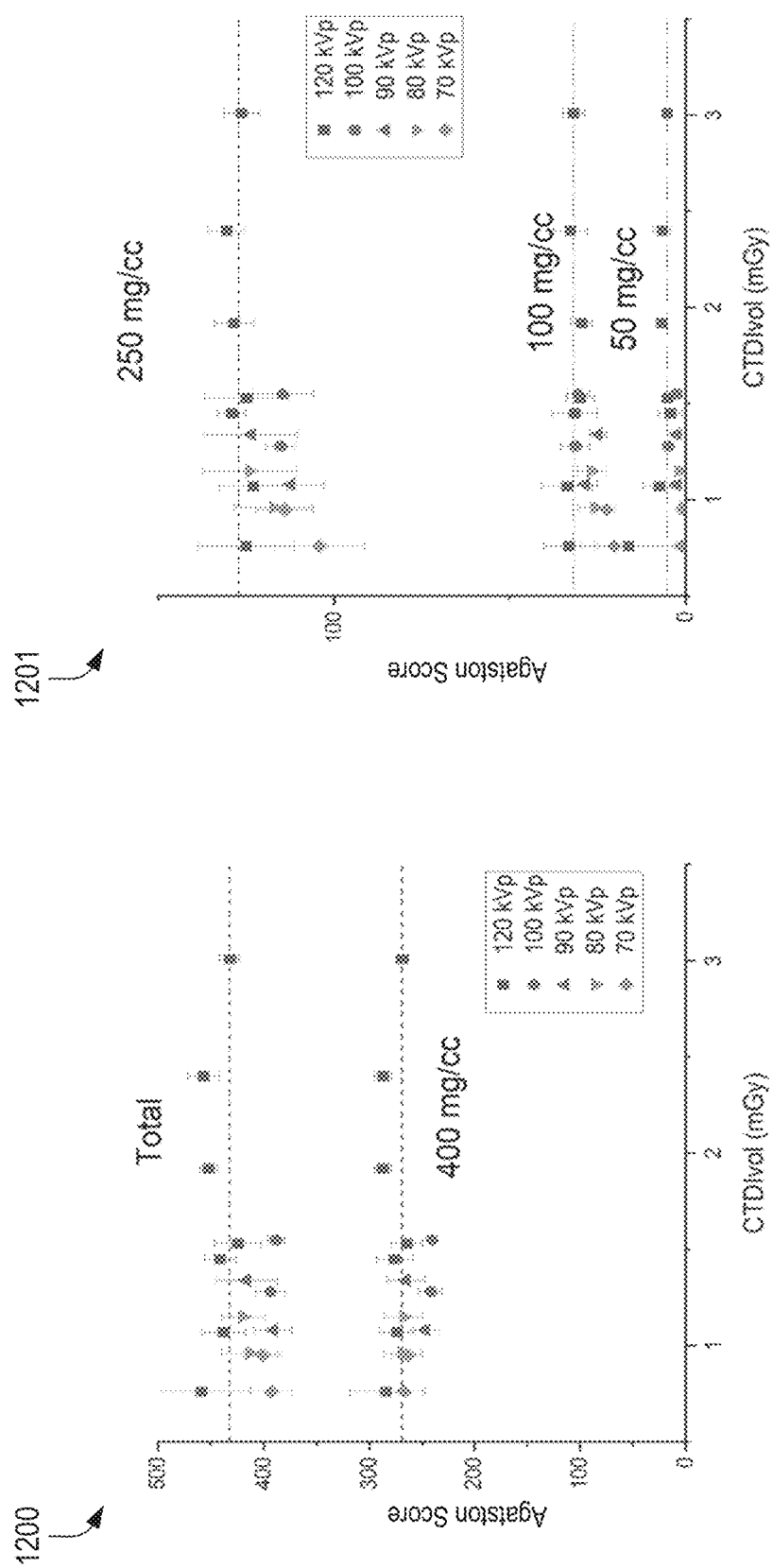
FIG. 12 is a set of charts depicting calcium scores and CTDI$_{vol}$ for scans at various kVp for a medium-sized sample, broken out by density of calcification, according to certain aspects of the present disclosure.

FIG. 12 is a set of charts 1200, 1201 depicting calcium scores and $CTDI_{vol}$ for scans at various kVp for a medium-sized sample, broken out by density of calcification, according to certain aspects of the present disclosure. The sample used for charts 1200, 1201 can be a medium-sized phantom. Charts 1200, 1201 are examples from scanning an example sample equating to an individual having an AP chest size of 22 cm and a LAT chest size of 32 cm.

Charts 1200, 1201 each depict several example scans performed at 120 kVp, 100 kVp, 90 kVp, 80 kVp, and 70 kVp. Chart 1201 depicts the regional calcium scores for calcification densities of 50 mg/cc, 100 mg/cc, and 250 mg/cc, whereas chart 1200 depicts the regional calcium score for a calcification density of 400 mg/cc and a total calcium score. For each density level, the dotted line represents the ground truth pinned to the 120 kVp scan at 3 mGy $CTDI_{vol}$.

As seen in charts 1200, 1201, many data points were taken for scans at kVp lower than 120 kVp, with dosages substantially lower than 3 mGy, while achieving the same or similar (e.g., within 10%) calcium scores as the ground truth. Further, the accuracy of the lower tube potential scans appear to even improve with higher-density calcifications.

Figure 13:
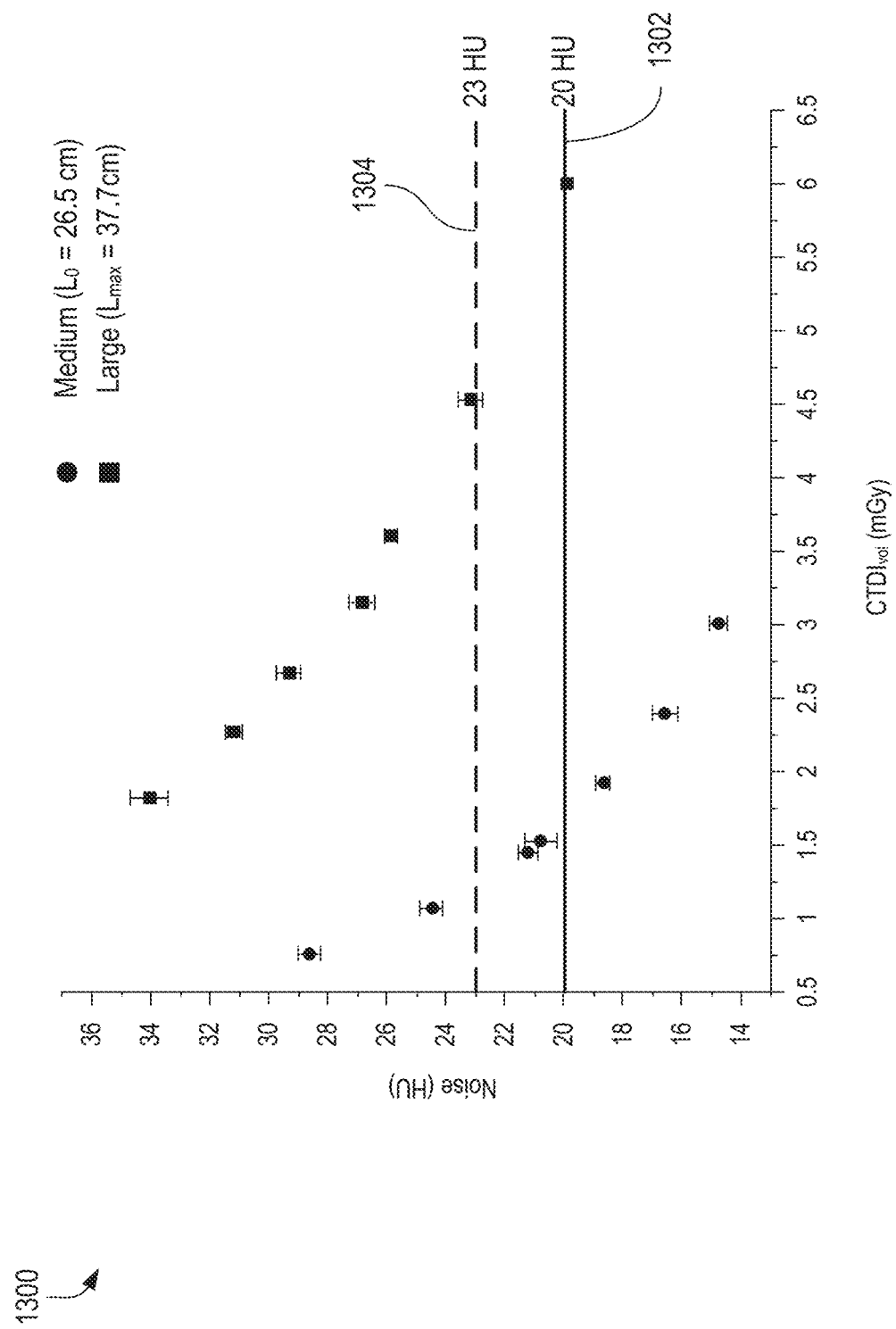
FIG. 13 is a chart depicting measured blood pool noise versus CTDI$_{vol}$ for two example samples, according to certain aspects of the present disclosure.

FIG. 13 is a chart 1300 depicting measured blood pool noise versus $CTDI_{vol}$ for two example samples, according to certain aspects of the present disclosure. Chart 1300 is used to depict the relationship between blood pool noise and $CTDI_{vol}$ for both medium-sized and large-sized samples. For each sampled $CTDI_{vol}$, the measurement of the blood pool results in a certain level of noise that deceases as the $CTDI_{vol}$ increases. For example, a $CTDI_{vol}$ of approximately 0.75 mGy on a medium sample achieves a noise level of approximately 28.6 HU, and a $CTDI_{vol}$ of approximately 2.6 mGy on a large sample achieves a noise level of approximately 29.3 HU.

The data from chart 1300 was collected using two thoracic phantoms (medium and large) with a moving heart module. Each phantom was scanned at 120 kVp (e.g., reference kVp) using a prospectively gated CACs with a CT imager at different $CTDI_{vol}$ levels (0.76-6 mGy). The motion for each phantom was driven by an ECG of 60 beats-per-minute. Noise measurements were made in the heart blood pool. The medium phantom had an effective diameter of approximately 26.5 cm ($L_0$) and its noise values are depicted as circular data points in chart 1300. The large phantom had an effective diameter of approximately 37.7 cm ($L_{max}$) and its noise values are depicted as square data points in chart 1300.

Thus, for any given maximum threshold of noise, the suitable $CTDI_{vol}$ values (e.g., lowest $CTDI_{vol}$ values that can be used and not exceed the maximum threshold of noise) can be determined for each phantom. Any suitable noise thresholds can be used, although two specific noise threshold approaches are described herein: a constant noise threshold approach and a Society of Cardiovascular CT (SCCT) recommended threshold approach. The constant noise threshold approach defined a maximum noise threshold of 20 HU for each phantom. The SCCT recommended threshold approach defined a maximum noise threshold of 20 HU for the size range in which the medium phantom falls and a maximum noise threshold of 23 HU for the size range in which the large phantom falls. The 20 HU threshold level is represented by line 1302 and the 23 HU threshold level is represented by line 1304.

A surrogate noise (SN) value was constructed as a function of the patient effective diameter and the $CTDI_{vol}$. SN was defined according to equation (9), in which L is the effective diameter and a is an experimentally derived constant:

$$SN = \frac{e^{\alpha L}}{\sqrt{CTDI_{vol}(L)}} \quad (9)$$

$CTDI_{vol}$ values were determined for each of the subject sizes (e.g., each of the medium and large phantoms or each of the selected small and large patients) using both the constant threshold approach and the SCCT recommended threshold approach. To derive the $CTDI_{vol}$, as a function of subject size within that range (e.g., the range between the two known sample sizes), it can be assumed that the threshold noise, and thus SN, varies linearly with the patient size.

Based on the results of the data, the derived formula for calculating $CTDI_{vol}$ can be expressed according to equation (10), referred to herein as the $CTDI_{vol,ref}$ (L) Model:

$$CTDI_{vol,ref}(L) = CTDI_{vol}(L_0) = \frac{e^{2\alpha(L-L_0)}}{\left[\left[L_{max} - L + \frac{T_{max}}{T_0}(L-L_0)\right] \middle/ (L_{max} - L_0)\right]^2} \quad (10)$$

where L is the effective diameter of the subject sample, $L_{max}$ is the effective diameter of the larger known sample size (e.g., large phantom or large clinical patient), $L_0$ is the effective diameter of the smaller known sample size (e.g., medium phantom or small clinical patient), $T_{max}$ is the threshold noise for the larger known sample size (e.g., large phantom or large clinical patient), $T_0$ is the threshold noise for the smaller known sample size (e.g., medium phantom or small clinical patient), and $\alpha$ is the experimentally derived constant from the previous equation. $CTDI_{vol}(L_0)$ is the $CTDI_{vol}$ value identified in chart 1300 at the $T_0$ threshold noise level.

This $CTDI_{vol,ref}$(L) Model, which is based on a reference kVp of 120 kVp, can be used to establish a new reference dose (e.g., $CTDI_{vol,ref}$) that is patient-size-dependent.

Under the constant threshold approach, $T_0=T_{max}=20$ HU. However, under the SCCT recommended threshold approach, $T_0=20$ HU and $T_{max}=23$ HU. As seen in chart 1300, under the constant thresholds, the $CTDI_{vol}$ for the medium and large phantoms are approximately 1.5 mGy and 6 mGy, respectively. Under the SCCT recommended thresholds, the $CTDI_{vol}$ for the medium and large phantoms are approximately 1.5 mGy and 4.5 mGy, respectively.

Figure 14:
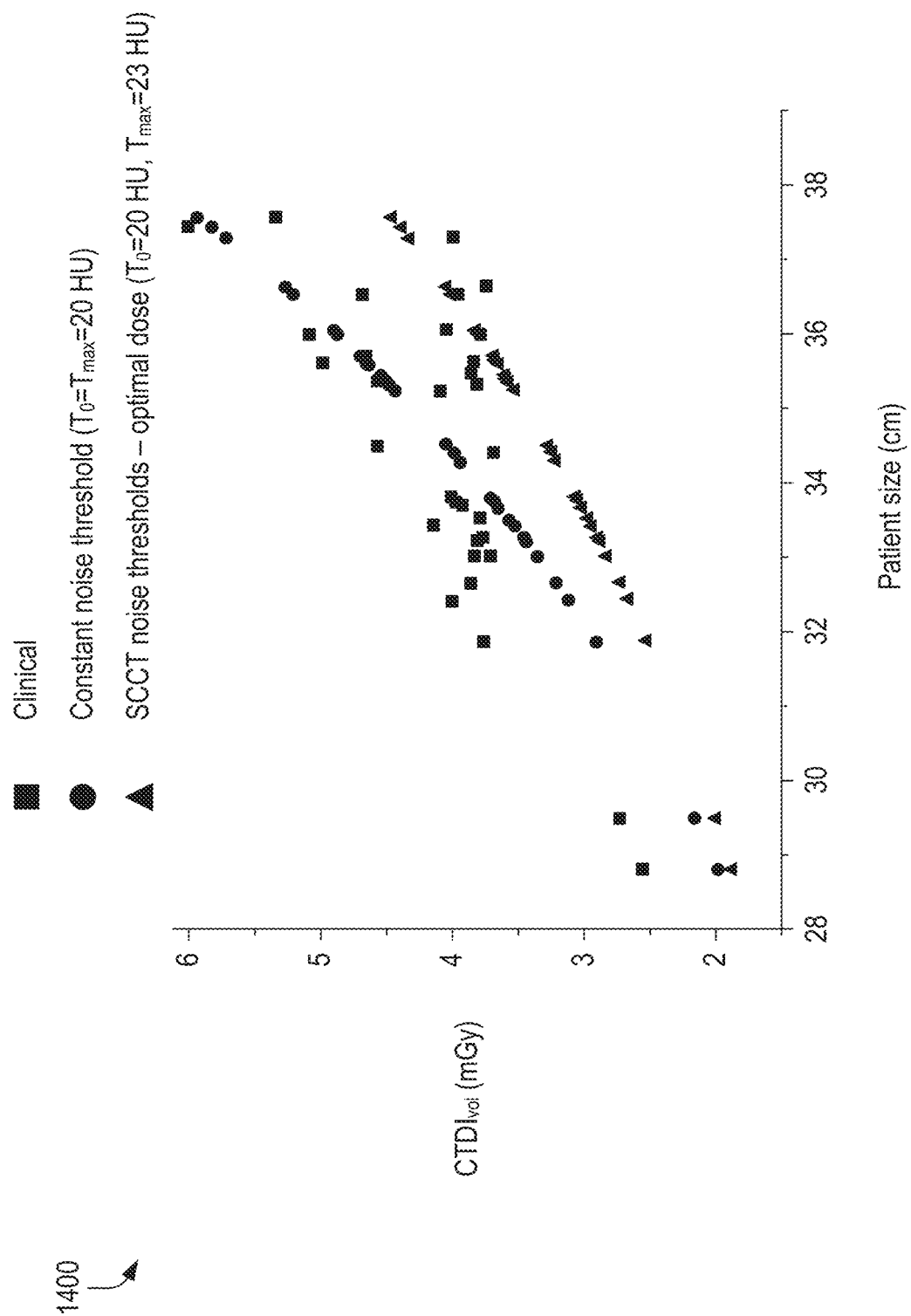
FIG. 14 is a chart comparing CTDI$_{vol}$ for medium-to-large patient sizes between clinical data, a constant noise threshold approach, and an SCCT noise threshold approach, according to certain aspects of the present disclosure.

FIG. 14 is a chart 1400 comparing $CTDI_{vol,ref}$ for medium-to-large patient sizes between clinical data, a constant noise threshold approach, and an SCCT noise threshold approach, using the two phantoms as the known sample sizes, according to certain aspects of the present disclosure. The data from chart 1400 is based on the experimental data and $CTDI_{vol,ref}$(L) Model referenced with respect to chart 1300 of FIG. 13.

In chart 1400, the square data points represent the $CTDI_{vol,ref}$ values plotted according to patient sizes for a set of 33 clinical cases using dose modulation with a reference effective mAs of 80. The round data points represent the $CTDI_{vol,ref}$ values per patient size as calculated from the $CTDI_{vol,ref}$(L) Model using the constant noise threshold approach (e.g., $T_0=T_{max}=20$ HU). The triangular data points represent the $CTDI_{vol,ref}$ values per patient size as calculated from the $CTDI_{vol,ref}$(L) Model using the SCCT recommended noise threshold approach (e.g., $T_0=20$ HU and $T_{max}=23$ HU).

As depicted in chart 1400 and according to the $CTDI_{vol,ref}$(L) Model, the doses to achieve the constant noise threshold (20 HU) were found more consistent with the observed patient doses, but switching to the SCCT variable thresholds resulted in a dose reduction of up to 25%. Thus, the $CTDI_{vol,ref}$(L) Model can be used to quantitatively model a prescribed patient-size-dependent optimal dose at standard 120 kVp for CACs. Further, this model can also serve as an optimal baseline for further dose reduction at lower kVp values.

Thus, by using the $CTDI_{vol,ref}$ (L) Model, an appropriate dose at the reference 120 kVp for an individual can be calculated based on the individual's own anatomy (e.g., the diameter of the individual's chest).

Figure 15:
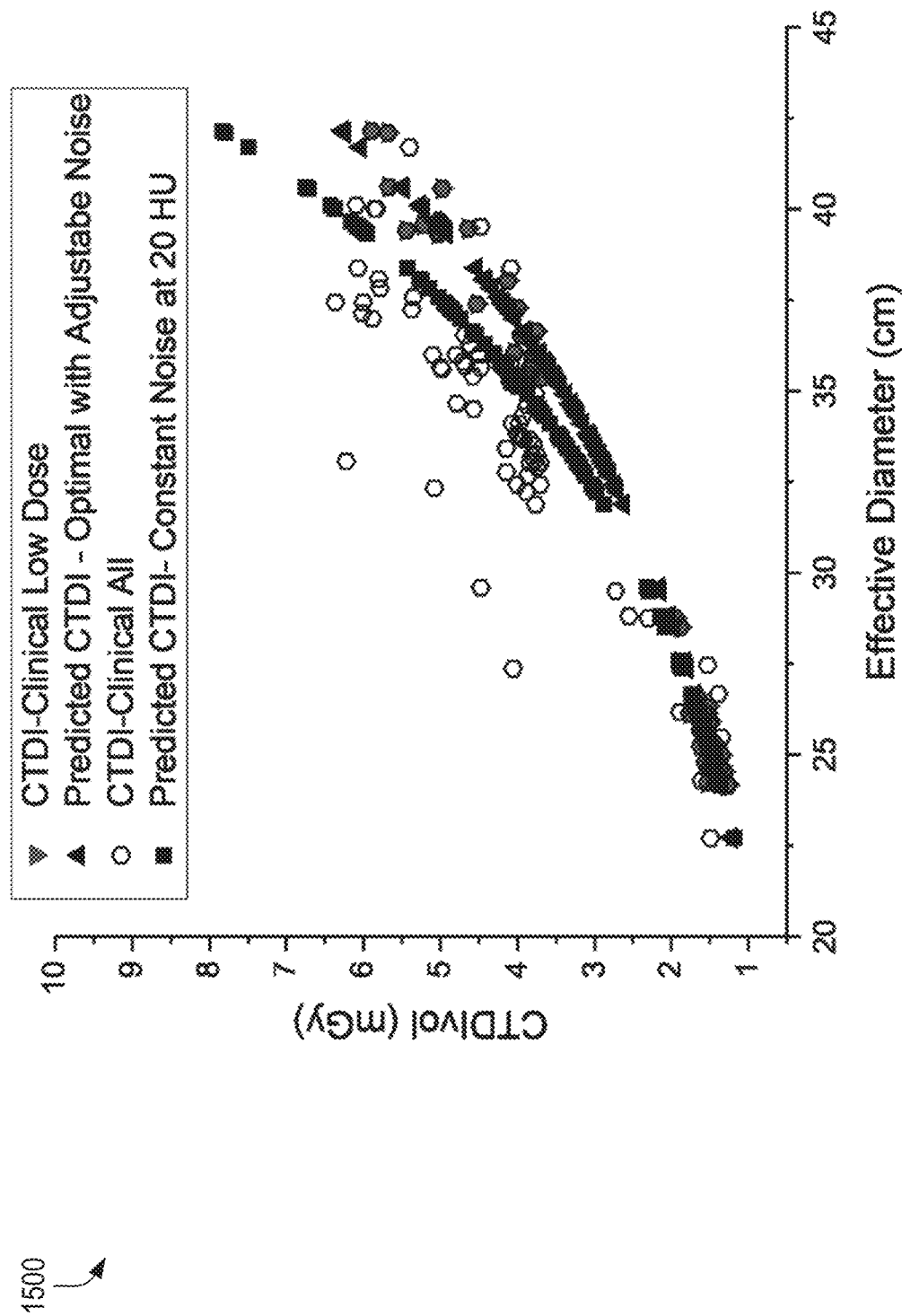
FIG. 15 is a chart comparing CTDI$_{vol}$ for small-to-large patient sizes between clinical data, a constant noise threshold approach, and an SCCT noise threshold approach, according to certain aspects of the present disclosure.

FIG. 15 is a chart 1500 comparing $CTDI_{vol,ref}$ for small-to-large patient sizes between clinical data, a constant noise threshold approach, and an SCCT noise threshold approach, using actual clinical patient data as the known sample sizes, according to certain aspects of the present disclosure. The data from chart 1500 is based on the $CTDI_{vol,ref}$ (L) Model referenced with respect to chart 1300 of FIG. 13 as applied to small patients (24.8 cm effective diameter) through large patients (40 cm effective diameter). The model used for chart 1500 was derived from a $CTDI(L_0)$ of 1.46 mGy (for an $L_0$ of 24.8 cm with a $T_0=20$ HU) and a $CTDI(L_{max})$ of 5.23 mGy (for an $L_{max}$ of 40.0 cm with a $T_{max}=23$ HU) based on the low dose clinical data.

In chart 1500, the hexagonal data points represent the $CTDI_{vol,ref}$ values plotted according to patient sizes for a set of 119 clinical cases using dose modulation with a reference effective mAs of 80. Of those 119 clinical cases, a subset of 48 cases of low dose usage, identified with inverted triangles within the hexagonal data point, lined up with the $CTDI_{vol,ref}$(L) Model within 10%. The square data points represent the $CTDI_{vol,ref}$ values per patient size as calculated from the $CTDI_{vol,ref}$(L) Model using the constant noise threshold approach (e.g., $T_0=T_{max}=20$ HU). The triangular data points represent the $CTDI_{vol,ref}$ values per patient size as calculated from the $CTDI_{vol,ref}$(L) Model using the SCCT recommended noise threshold approach (e.g., $T_0=20$ HU and $T_{max}=23$ HU) ("Optimal with Adjustable Noise").

The data from chart 1500 show a room of dose reduction of 20% on average, with greater dose reduction available for larger patients.

As depicted in chart 1500 and according to the $CTDI_{vol,ref}$(L) Model, the doses to achieve the constant noise threshold (20 HU) were found more consistent with the observed patient doses, but switching to the SCCT variable thresholds resulted in a dose reduction of up to 25%. Thus, the $CTDI_{vol,ref}(L)$ Model can be used to quantitatively model a prescribed patient-size-dependent optimal dose at standard 120 kVp for CACs. Further, this model can also serve as an optimal baseline for further dose reduction at lower kVp values.

Thus, by using the $CTDI_{vol,ref}(L)$ Model, an appropriate dose at the reference 120 kVp for an individual can be calculated based on the individual's own anatomy (e.g., the diameter of the individual's chest).

Figure 16:
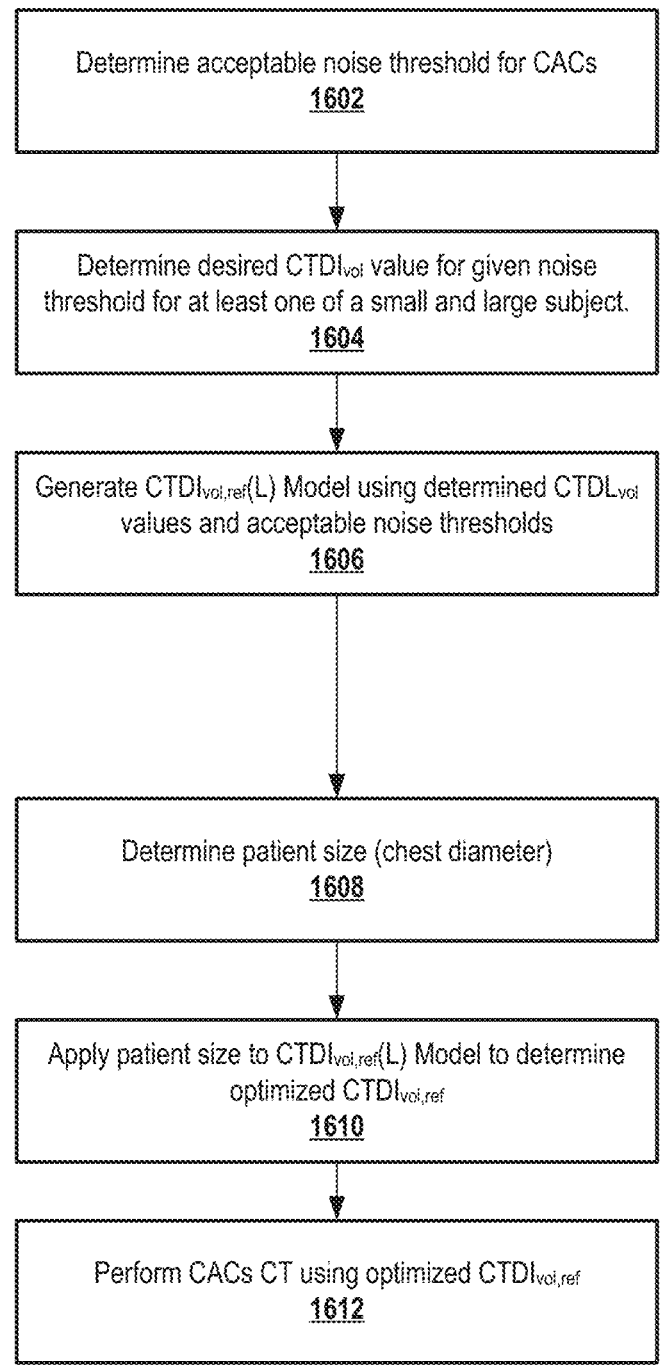
FIG. 16 is a flowchart depicting a process for generating and using a CTDI$_{vol}$(L) Model, according to certain aspects of the present disclosure.

FIG. 16 is a flowchart depicting a process 1600 for generating and using a $CTDI_{vol,ref}(L)$ Model, according to certain aspects of the present disclosure. Process 1600 can be performed by system 100 of FIG. 1, or any other suitable system.

At block 1602, one or more acceptable noise thresholds can be determined for use in CACs, according to certain aspects of the present disclosure. The one or more acceptable noise thresholds can be based on constant noise thresholds (e.g., a single noise threshold irrespective of diameter of the subject) or variable noise thresholds (e.g., different noise thresholds based on diameter of the subject). In some cases, the acceptable noise thresholds can be SCCT recommended noise thresholds.

At block 1604, the desired $CTDI_{vol}$ value can be determined for at least one of a smaller subject and a larger subject. The smaller subject is smaller in diameter than the larger subject. For example, the smaller subject and larger subject can be the medium-sized and large-sized phantoms described with reference to FIGS. 13-14. The desired $CTDI_{vol}$ for a given subject can be based on the acceptable noise threshold for that subject as determined at block 1602. In some cases, the desired $CTDI_{vol}$ is the lowest possible $CTDI_{vol}$ that will not cause the acceptable noise threshold to be exceeded. In some cases, the desired $CTDI_{vol}$ is offset from such a lowest possible $CTDI_{vol}$, such as being offset by a given value of mGy, being offset by a given percentage, or being the nearest $CTDI_{vol}$ of a set of available $CTDI_{vol}$ that will achieve sub-threshold noise levels. The $CTDI_{vol}$ levels for a subject can be determined using any suitable technique, such as comparison to experimental data acquired for the subject at various $CTDI_{vol}$ levels.

At block 1606, a $CTDI_{vol,ref}(L)$ Model is generated using the determined $CTDI_{vol}$ level(s) from block 1604 and the determined acceptable noise thresholds from block 1602. The $CTDI_{vol,ref}(L)$ Model can take the form of the equation (11):

$$CTDI_{vol,ref}(L) = CTDI_{vol}(L_0) = \frac{e^{2\alpha(L-L_0)}}{\left[L_{max} - L + \frac{T_{max}}{T_0}(L-L_0)\right]/(L_{max}-L_0)\right]^2}, \quad (11)$$

where L is a dependent variable and the effective diameter of a given subject to be evaluated, $L_{max}$ is the effective diameter of the larger subject, $L_0$ is the effective diameter of the smaller subject, $T_{max}$ is the threshold noise for the larger subject, $T_0$ is the threshold noise for the smaller subject, and $\alpha$ is an experimentally derived constant. $CTDI_{vol}(L_0)$ is the $CTDI_{vol}$ value for the smaller subject as determined at block 1604.

In some cases, process 1600 can end at block 1606, resulting in the creation of a model suitable for determining $CTDI_{vol,ref}$ based on a given effective diameter of a subject. In some cases, however, process 1600 can proceed at block 1608. Block 1608 can follow block 1606 by any suitable length of time, such as minutes, days, months, years, or the like. In some cases, process 1600 can start at block 1608 and not include blocks 1602, 1604, 1606, in which case the $CTDI_{vol,ref}(L)$ Model that is used can be accessed from a preprogrammed memory.

At block 1608, patient size is determined, such as via measurement or accessing electronic medical records. The patient size can be a chest size, such as an effective diameter of the chest of the patient.

At block 1610, the patient size is applied to a $CTDI_{vol,ref}(L)$ Model to determine the optimized $CTDI_{vol,ref}$ to use for that patient. The optimized $CTDI_{vol,ref}$ can be the most optimum $CTDI_{vol,ref}$ or a near-optimum $CTDI_{vol,ref}$. The optimized $CTDI_{vol,ref}$ can be lower than a standard $CTDI_{vol,ref}$ under traditional CACs. The $CTDI_{vol,ref}(L)$ Model can be the $CTDI_{vol,ref}(L)$ Model from block 1606.

At block 1612, CACs CT can be performed using the optimized $CTDI_{vol,ref}$ from block 1610. Performing the CACs CT can occur similarly as described with reference to process 800 of FIG. 8, but using the optimized $CTDI_{vol,ref}$ as the reference dose from which an appropriate dose is based.

Referring now to FIGS. 17-22, aspects of the present disclosure relate to systems and methods for modulating the dose during CACs performed at 120 kVp to satisfy a predetermined noise threshold. The volume CT dose index $CTDI_{vol}$ for a patient is a function of a variety of different parameters, as shown by equation (12):

$$CTDI_{vol} = f(\sigma, D_h, t, K, H) \quad (12)$$

Here, $\sigma$ is the noise in the descending aorta, $D_h$ is the effective chest diameter of the patient in the heart region, t represents the slice thickness of the CT scan, K represents the reconstruction algorithm used for the CT scan, and H represents aspects of the hardware implementation of the CT scan related to detection, collimator design and scatter reduction, and the x-ray source(s).

For CACs, the slice thickness and the reconstruction algorithm do not change when performed on the same scanner, and thus equation (12) can be simplified:

$$CTDI_{vol} = g(\sigma, D_h) \quad (13)$$

To obtain the function g in simplified equation (13), a phantom experiment using a variety of phantom sizes and $CTDI_{vol}$ values was conducted, and the corresponding noise was measured. For the phantom experiment, the simplified equation is given by $$CTDI_{vol} = g(\sigma, D_p) \quad (14)$$

where $D_p$ is the diameter of the phantom. Typically, phantoms are made of uniform materials that differ significantly from the heart region of a human patient. Thus, the relationship between the diameter of a phantom of a specific material and the effective chest diameter of a patient needs to be obtained. After that relationship is found, $CTDI_{vol}$ based on a threshold noise level $\sigma_t$ can be determined.

In the phantom experiment, a Mercury 4.0 phantom composed of five circular disks having diameters ranking from 16 cm to 36 cm was used. A 4 cm thick tapered transitional region was positioned between adjacent disks. The base material was made of polyethylene (nominal 90 HU at 120 kVp), and each disk contained a uniform section with a thickness of 3 cm. Inserts of various contrast materials formed non-uniform portions that were not utilized.

The phantom study was conducted on a dual-source CT (Siemens Somatic Force, syngo CT VB20A, Siemens Healthcare GmbH). All images were acquired with axial mode using the coronary calcium score protocol at 120 kVp. The dual-source mode and smart beam collimation up to 96×0.6 mm were utilized to cover the scan length. A gated window of 40% peak-to-peak (R-R) was employed with a simulated ECG of 60 beats per minute. The images were reconstructed to 3 mm thickness using the filtered back-projection algorithm. The reconstruction diameter was set to 18 cm as typically used in clinical practice. The tube current (mA) was manually adjusted to eight different $CTDI_{vol}$ values (0.34 mGy to 18.7 mGy). Three repeats were performed for each mA setting.

Noise measurements were made by using ImageJ (v1.52a) (NIH). Circular regions of interest (ROI) of 15 mm in diameter were placed in the uniform sections of the disk images. The noise was obtained by averaging the standard deviations from the four contiguous slices. The images near the longitudinal center in each tapered region were also used for additional noise data at the varied diameters. The noise measurements were averaged from two consecutive slices in the tapered regions. The final results were averaged from the three repeated acquisitions. The data analysis was made using Origin 2020b (OriginLab Corporation). The noise was plotted against the phantom diameter and CTDIvol. The total number of data points from the ensemble of noise-diameter-CTDIvol was 18×8=144. The least square non-linear surface fit was performed using equation (15):

$$\sigma = A e^{BD_p} * CTDI_{vol}{}^c, \quad (15)$$

where A, B, and C were to be determined from the fitting.

Figure 17:
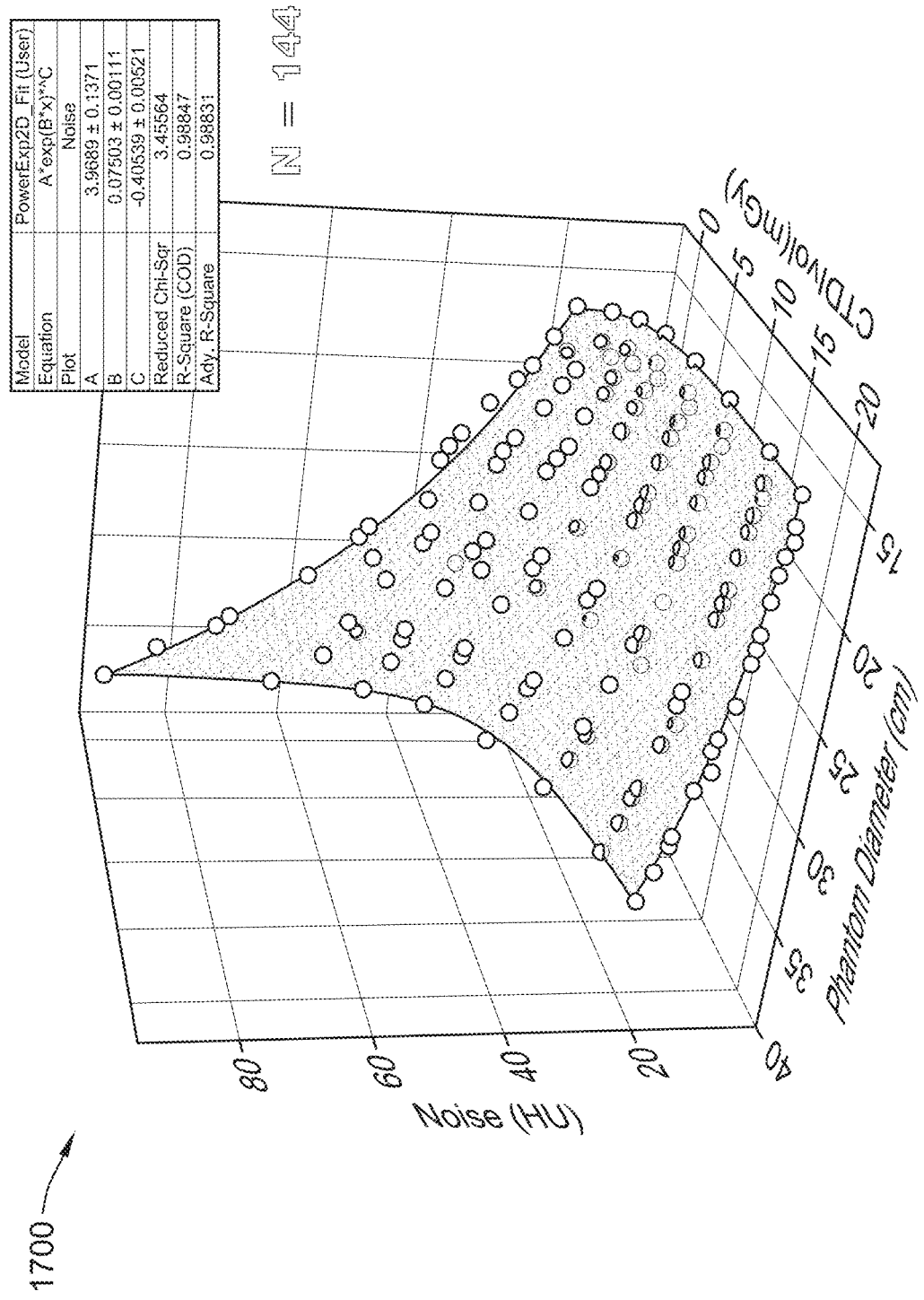
FIG. 17 is a plot depicting measured blood pool noise versus phantom diameter and CTDI$_{vol}$, according to certain aspects of the present disclosure.

FIG. 17 shows a plot 1700 of the noise (measured in HU) against phantom diameter (measured in cm) and the volume CT dose index (measured in mGy). This data was well-fitted to equation (15) with the following parameter values: A=3.969, B=0.075, and C=−0.405, with $R^2$=0.988. Thus, in some implementations, the constants A, B, and C can have these values.

To find the specific relationship between the polyethylene phantom diameter $D_p$ and the patient effective chest diameter in the heart region $D_h$, the attenuation equivalence over the cross-area from the phantom to clinical chest size was applied. The mechanism is similar to finding the water equivalent diameter from the patient anatomy. This leads to equation (16):

$$D_p = D_h \sqrt{\frac{\overline{HU_h} + 1000}{\overline{HU_p} + 1000}}, \quad (16)$$

where $\overline{HU_h}$ and $\overline{HU_p}$ are the average Hounsfield unit in the chest (at the heart level) and in the phantom, respectively.

Figure 18:
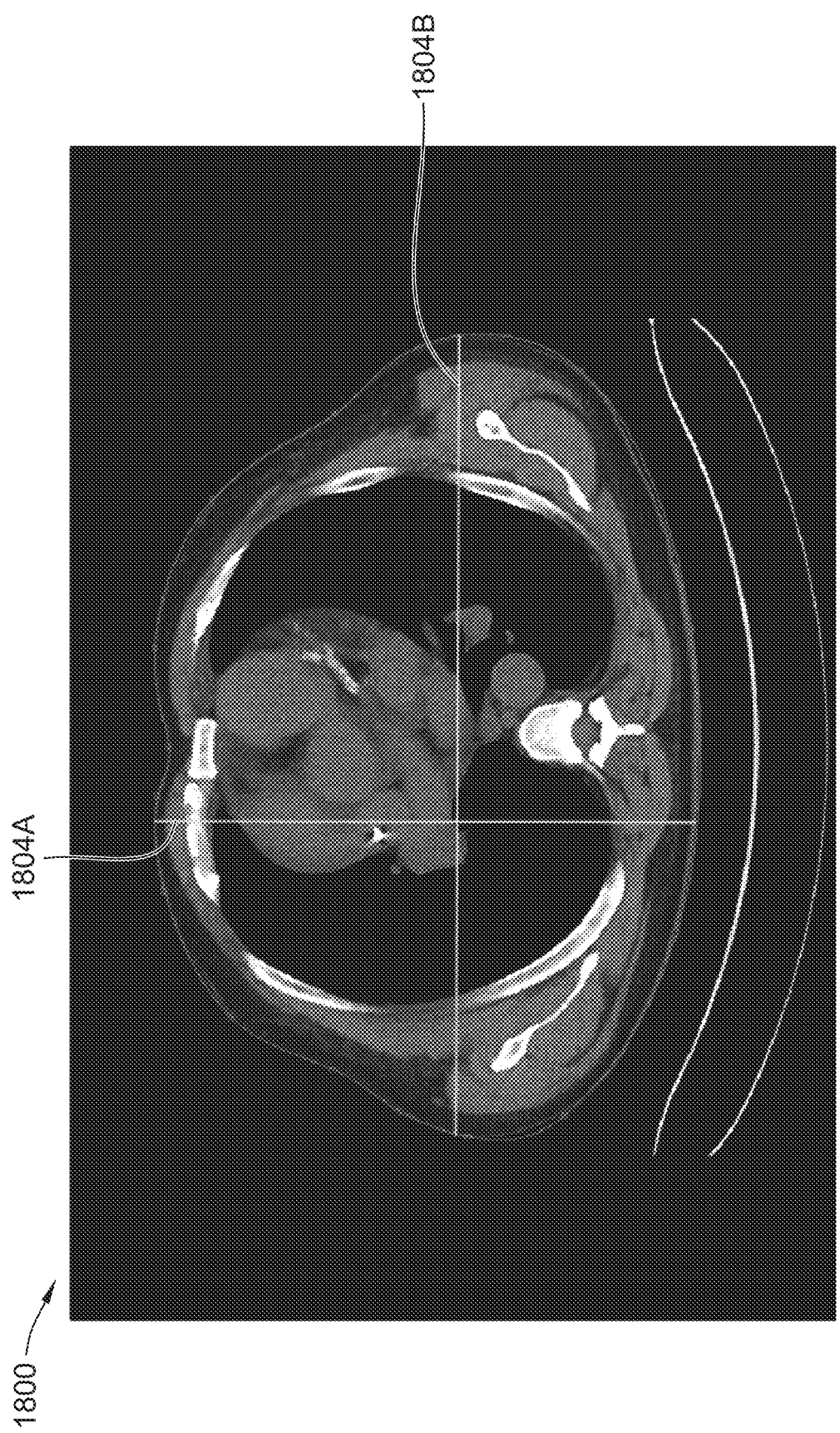
FIG. 18 is a CT image of a chest cavity, according to certain aspects of the present disclosure.

The typical reconstruction field of view for CACs studies is only about 18 cm, therefore the axial images of the entire chest were not available for the measurement of $\overline{HU_h}$. Since the relation of $D_p$ and $D_h$ is not dependent on CAC scan specifics, separate clinical chest CT studies without iodine contrast (N=140) were retrospectively extracted from a Siemens Flash CT scanner, and chest cavity CT images were obtained from the clinical chest CT studies. FIG. 18 shows an example chest cavity CT image 1800. The general outline of the chest cavity is shown by border 1802, the lateral dimension of the chest cavity is shown by axis 1804A, and the anterior-posterior dimension of the chest cavity is shown by axis 1804B. In each exam, the effective diameter $D_h$ was obtained from the geometric average of the lateral and anterior-posterior dimensions. The measurements were made at the longitudinal level where the coronary arteries start to branch out from the ascending aorta. The level approximately corresponds to the mid-line of the CACs scan's length. The $\overline{HU_h}$ was obtained from the average CT number within the carefully contoured chest areas of the extracted clinical chest CT studies. The $\overline{HU_p}$ was obtained from the average CT number of the Mercury phantom images at different diameters. For each $D_h$ (e.g., for the effective chest diameter $D_h$ of each of the N=140 clinical chest CT studies), a corresponding $D_p$ was derived using the above equation.

Figure 19:
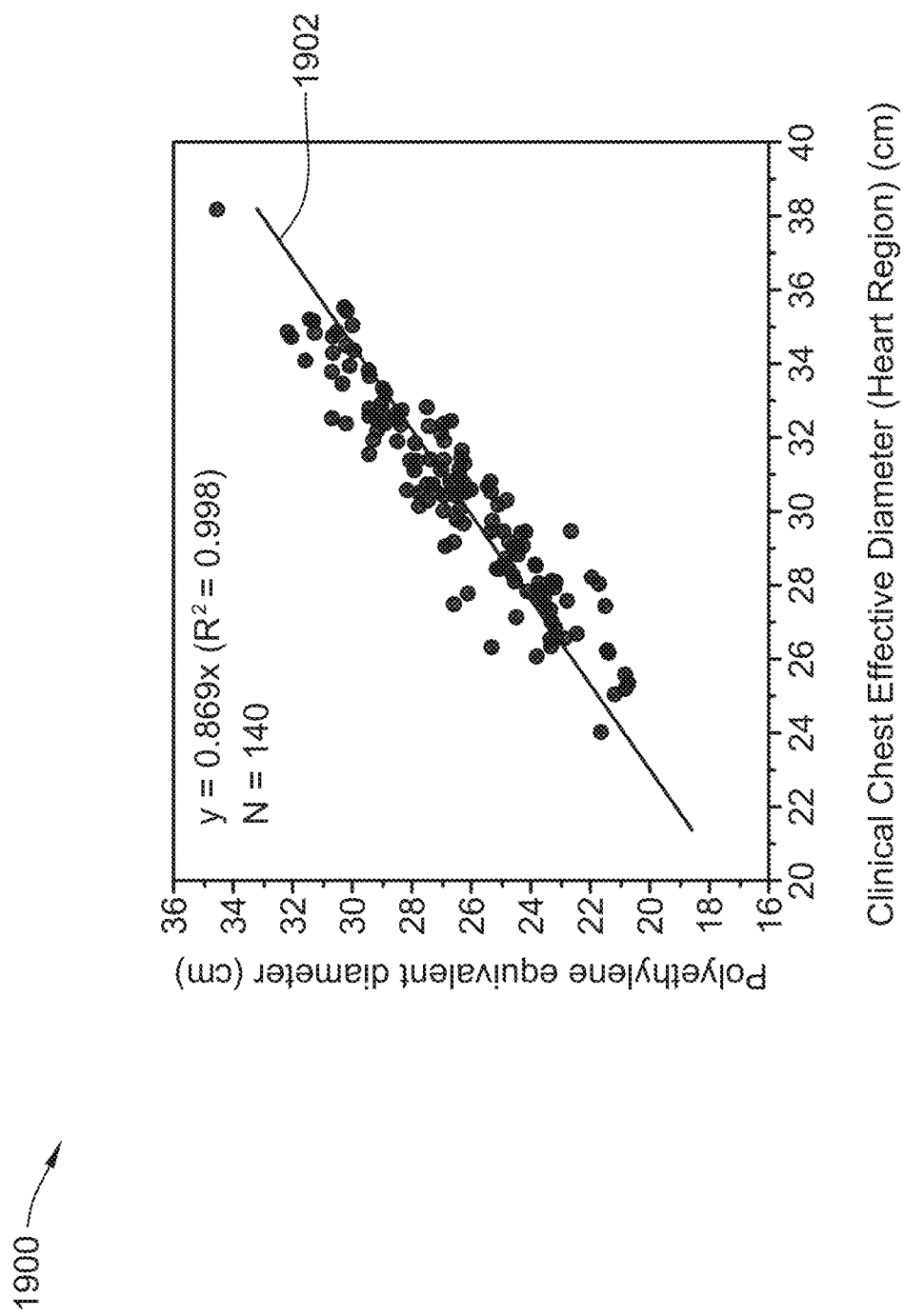
FIG. 19 is a plot depicting phantom diameter versus effective chest diameter, according to certain aspects of the present disclosure.
Figure 20:
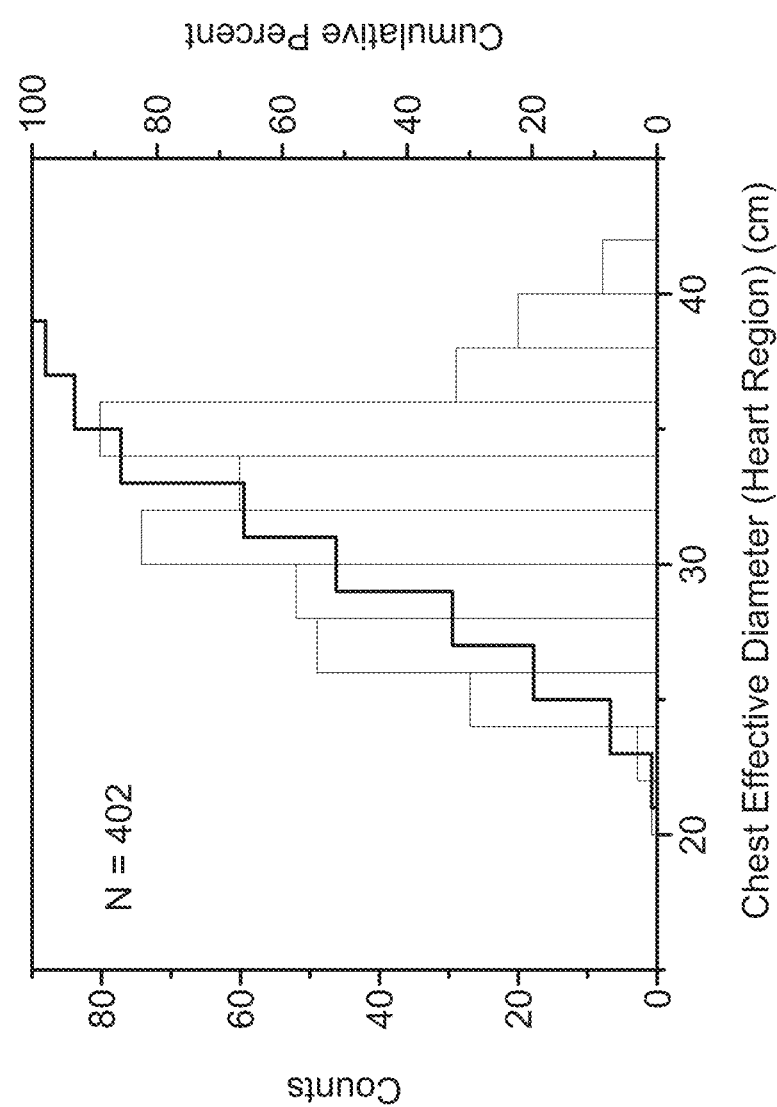
FIG. 20 is a plot depicting the count of different effective chest diameters from clinical data, according to aspects of the present disclosure.

FIG. 19 shows a plot 1900 of phantom diameter versus effective chest diameter for the 140 clinical chest CT studies. A least square linear fit line 1902 with a slope off 0.869 was found to have the best correlation, with $R^2$=0.998. Using this data, the relationship between the effective patient chest diameter at the heart region $D_h$ and the effective phantom diameter can be expressed as $D_p = q(D_h) = 0.869 * D_h$. Thus, in some implementations, the effective chest diameter of the patient at the heart region can be expressed this manner.

If equation (15) (e.g., the model $\sigma = A e^{BD_p} * CTDI_{vol}{}^c$) is valid, the noise threshold $\sigma_t$ can be set for any patient size (e.g., any effective chest diameter $D_h$) using the exponential form $\sigma_t = K e^{\lambda D_h}$. If two separate noise thresholds $\sigma_{t1}$ and $\sigma_{t2}$ are used for two different discrete effective chest diameter thresholds $d_{h1}$ and $d_{h2}$, then the parameters K and $\lambda$ can be derived according to equations (17) and (18):

$$\lambda = \frac{\ln\left(\frac{\sigma_{t2}}{\sigma_{t1}}\right)}{d_{h2} - d_{h1}}, \text{ and} \quad (17)$$

$$K = \frac{\sigma_{t2}}{e^{\lambda d_{h2}}}. \quad (18)$$

If $d_{h1}$ and $d_{h2}$ represent effective chest diameter thresholds of medium and large patients (e.g., a first threshold size and a second threshold size), than the threshold noise $\sigma_t$ can be expressed according to equation (19):

$$\sigma_t = \begin{cases} \sigma_{t1}, & \text{if } D_h \leq d_{h1} \\ K e^{\lambda D_h}, & \text{if } d_{h1} \leq D_h \leq d_{h2} \\ K e^{\lambda D_h} (\text{option 1}), & \text{if } D_h > d_{h2} \\ \sigma_{t2} (\text{option 2}), & \text{if } D_h > d_{h2} \end{cases} \quad (19)$$

If the threshold noise $\sigma_t$ is used in equation (15), then the optimal volume CT dose index for that threshold noise $\sigma_t$ as a function of the effective chest diameter $D_h$ can be expressed according to equation (20):

$$CTDI_{vol,opt}(D_h) = \left(\frac{A e^{Bq(D_h)}}{\sigma_t}\right)^{-\frac{1}{C}}, \quad (20)$$

where $D_p$ is replaced with $q(D_h)$, which can be obtained from equation (16) by incorporating clinical data. Thus, $q(D_h)$ is a function representing the effective chest diameter of the patient relative to a reference size (e.g., the size of the phantoms). By selecting appropriate predetermined noise thresholds $\sigma_1$, $\sigma_2$ and effective chest diameter thresholds $d_{h1}$, $d_{h2}$, the parameters λ and K can be obtained using equations (17) and (18). The noise threshold $\sigma_t$ for a specific patient can then be selected using equation (19) based on the parameters λ and K, the effective chest diameter thresholds $d_{h1}$ and $d_{h2}$, and the effective chest diameter of the patient. Finally, the optimal volume CT dose index can be determined for the patient using equation (20), using known values of the parameters A, B, and C, as well as the known function $q(D_h)$.

In some implementations, the noise thresholds are $\sigma_{t1}$=20 HU and $\sigma_{t2}$=23 HU. In these implementations, equation (19) is consistent with the recommendation of The Society of Cardiovascular CT (SCCT) for continuous threshold values for any effective chest diameter $D_h$ between $d_{h1}$ and $d_{h2}$. If the effective chest diameter D is larger than $d_{h2}$, a first option for $\sigma_t$ is to extrapolate the exponential form of $\sigma_t$ with the larger effective chest diameter, or to simply just use $\sigma_t = \sigma_{t2}$.

In some implementations, $d_{h1}$=30 cm and $d_{h2}$=36 cm. These values are consistent with databases of patient effective chest size. For example, FIG. 20 includes a plot 2000 that shows the count of various different patient effective chest diameter values (measured in cm) obtained from a plurality of retrospective studies. Plot 2000 shows two large peaks generally aligning with patient effective chest diameters of 30 cm and 36 cm. These thresholds also align with data from the National Radiology Dose Index Registry provided by the American College of Radiology, as well as with the SCCT's examples of medium and large patients' lateral widths.

In implementations where $\sigma_{t1}$=20 HU and $\sigma_{t2}$=23 HU, the parameters in equations (17) and (18) can be obtained as λ=0.023 HU and K=9.943 $cm^{-1}$. The size-dependent noise threshold (e.g., the patient-specific $\sigma_t$) can then be determined for a variety of different effective chest diameter, as shown in plot 2100 of FIG. 21A. Plot 2100 includes a first data series 2102A showing the patient-specific noise thresholds $\sigma_t$ versus patient effective chest diameter when option 1 of equation (19) is used for patient effective chest diameters larger than the second threshold $d_{h2}$, and a second data series 2102B showing the patient-specific noise thresholds $\sigma_t$ versus patient effective chest diameter when option 2 of equation (19) is used for patient effective chest diameters larger than the second threshold $d_{h2}$. As can be seen, the noise threshold $\sigma_t$ only differs once the patient effective chest diameter is greater than the second thresholds $d_{h2}$.

Figure 21A:
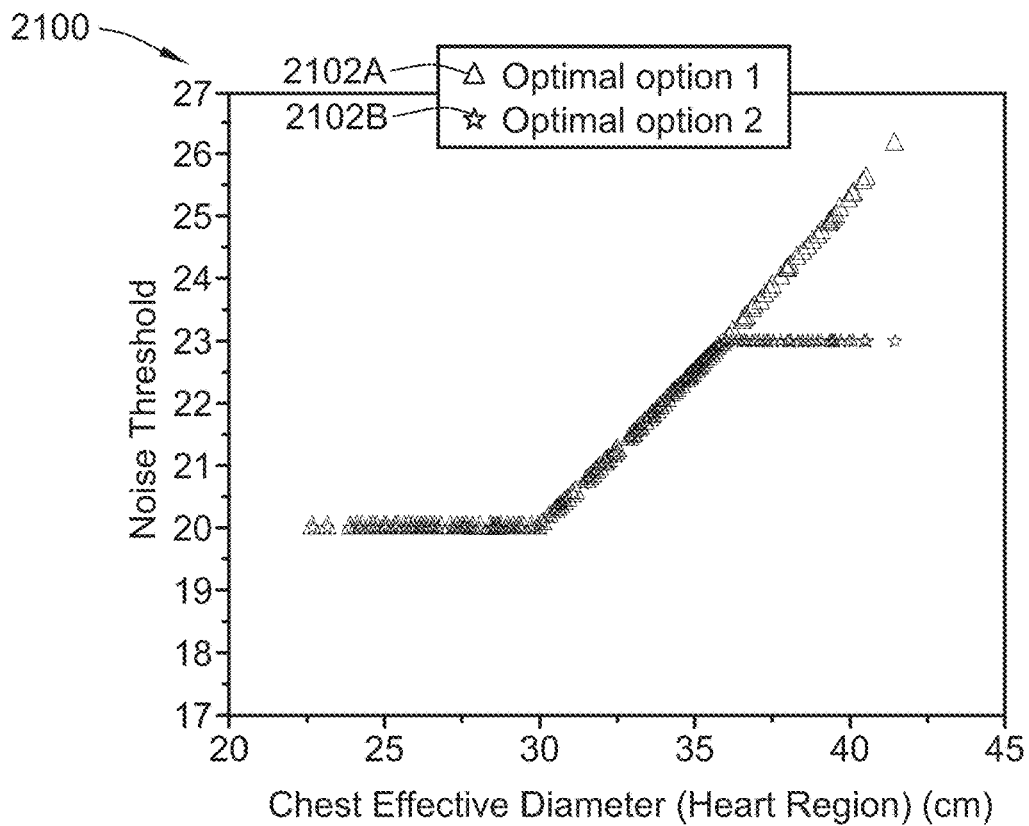
FIG. 21A is a plot depicting a noise threshold $\sigma_t$ versus effective chest diameter, according to aspects of the present disclosure.
Figure 21B:
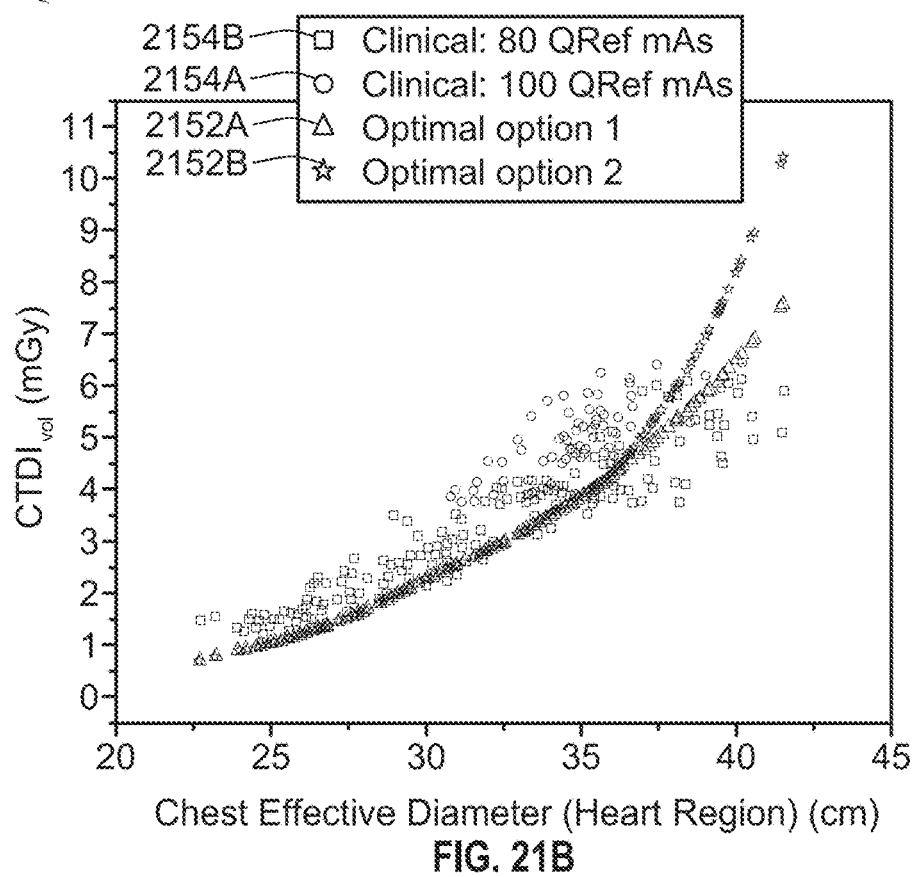
FIG. 21B is a plot depicting CTDI$_{vol,opt}$ versus effective chest diameter, according to aspects of the present disclosure.

Once the patient-specific noise thresholds $\sigma_t$ is determined, the optimal volume CT dose index can be determined according to equation (20), as shown for example in plot 2150 of FIG. 21B. Plot 2150 includes a first data series 2150A showing the optimal volume CT dose index (measured in mGy) versus patient effective chest diameter when option 1 of equation (19) is used for patient effective chest diameters larger than the second threshold $d_{h2}$ (corresponding to the first data series 2102A of FIG. 21A), and a second data series 2150B showing the optimal volume CT dose index (measured in mGy) versus patient effective chest diameter when option 2 of equation (19) is used for patient effective chest diameters larger than the second threshold $d_{h2}$ (corresponding to the second data series 2102B of FIG. 21A). The optimal volume CT dose index values of the first data series 2150A and the second data series 2150B were determined using numerical values of the parameters A, B, and C (such as the values determined with respect to FIG. 19), as well as the numerical value of the function $q(D_h)$ in equation (such as the value determined with respect to FIG. 19) in equation (19).

Plot 2150 also includes a reference data series 2152 showing clinically recorded optimal volume CT dose index values for a dose modulation scheme with tube current and exposure time of 80 mAs, and a reference data series 2154 showing clinically recorded optimal volume CT dose index values for a dose modulation scheme with tube current and exposure time of 100 mAs. As can be seen, the optimal volume CT dose index values determined according to aspects of the present disclosure compare favorably to dose modulation schemes that utilize varying tube current and exposure times.

Figure 22:
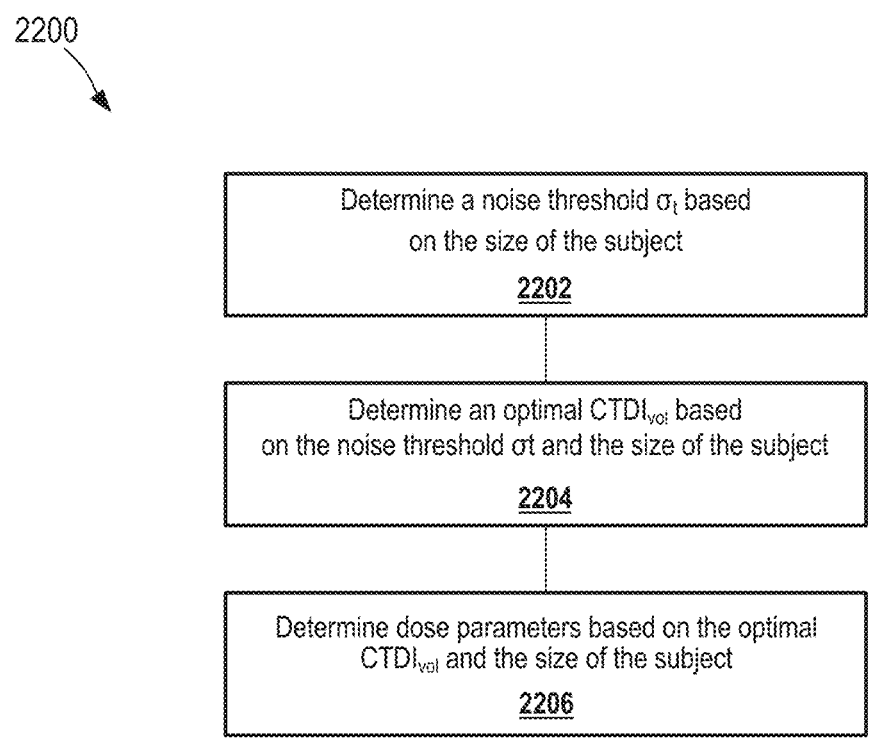
FIG. 22 is a flowchart depicting a process for determining dose parameters for a coronary calcium score based on patient size.

FIG. 22 shows a flowchart of a method 2200 for measuring cardiac health of a patient. Method 200 can be implemented as part of a CT scan (such as a CAC test). At step 2202 of method 2200, a noise threshold $\sigma_t$ is determined for the patient that is based at least in part on the size of the patient. In some implementations, the size of the patient is the effective chest diameter of the patient (such as at the heart region), as discussed herein. However, other measures of patient size can also be used.

In some implementations, the noise threshold $\sigma_t$ is based at least in part of the size of the patient relative to one or more threshold sizes. In some of these implementations, the noise threshold $\sigma_t$ is based at least in part on the size of the patient relative to a first threshold size and a second threshold size. If the patient size is less than or equal to the first threshold size value, than the noise threshold $\sigma_t$ is equal to a first noise value. If the patient size is greater than or equal to the first threshold size value and less than or equal to the second threshold size value, than the noise threshold $\sigma_t$ is equal to a second noise value. If the patient size is greater than the second threshold size value, than the noise threshold $\sigma_t$ is equal to a third noise value. In some implementations, the noise threshold $\sigma_t$ is determined according to equation (19) above.

At step 2202, the optimal CT dose index $CTDI_{vol,opt}$ is determined based at least in part on the determined noise threshold $\sigma_t$ and the size of the patient. In some implementations, the optimal CT dose index $CTDI_{vol,opt}$ is determined according to equation (20) above. At step 2206, dose parameters are determined based on the optimal CT dose index $CTDI_{vol,opt}$. In some implementations, the dose parameters include the tube current and the exposure time used during the CT scan. In some implementations, the peak tube kilovoltage during the CT scan is 120 kV, and the tube current and exposure time are determined based on a 120 kV peak kilovoltage and the determined optimal CT dose index $CTDI_{vol,opt}$.

Thus, method 2200 provides an optimal dose modulation scheme for a CAC scoring CT at a standard peak tube kilovoltage of 120 kV. The optimal CT dose index $CTDI_{vol,opt}$ is determined based on a specific noise threshold that is suitable for CACs that can be adapted based on the size of the patient.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

While various embodiments of the present invention have been described above, it should be understood that they have been presented by way of example only, and not limitation. Numerous changes to the disclosed embodiments can be made in accordance with the disclosure herein, without departing from the spirit or scope of the invention. Thus, the breadth and scope of the present invention should not be limited by any of the above described embodiments.

The terminology used herein is for the purpose of describing particular embodiments only, and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

As used below, any reference to a series of examples is to be understood as a reference to each of those examples disjunctively (e.g., "Examples 1-4" is to be understood as "Examples 1, 2, 3, or 4").

Example 1 is a method for measuring cardiac health, the method comprising: determining a target peak kilovoltage for driving a radiation source of a medical scanner, wherein the target peak kilovoltage is less than 120 kV; determining an appropriate dose based on the target peak kilovoltage, wherein the appropriate dose is determined to achieve a contrast-to-noise ratio equal to a contrast-to-noise ratio associated with a defined target peak kilovoltage of 120 kV; amd determining dose parameters based on the appropriate dose Example 2 is the method of example(s) 1, further comprising driving the medical scanner using the target peak kilovoltage and the dose parameters.

Example 3 is the method of example(s) 1 or 2, wherein the target peak kilovoltage is at or between 70 kV and 100 kV.

Example 4 is the method of example(s) 1-3, wherein the medical scanner is a computed tomography (CT) scanner.

Example 5 is the method of example(s) 1-4, wherein determining the appropriate dose comprises applying a reducing factor to a reference dose, wherein the reference dose is associated with the defined target peak kilovoltage of 120 kV.

Example 6 is the method of example(s) 5, wherein determining the appropriate dose comprises applying the formula $$CTDI_{vol} = \left(\frac{kVp_{target}}{120}\right)^{1.246} * CTDI_{vol,ref}$$

where $CTDI_{vol}$ is the appropriate dose in mGy, $kVp_{target}$ is the target peak kilovoltage in kV, and $CTDI_{vol,ref}$ is the reference dose in mGy.

Example 7 is the method of example(s) 5-6, wherein determining the appropriate dose includes determining the reference dose, and wherein determining the reference dose includes: determining a chest size of a subject; and calculating the reference dose using the chest size.

Example 8 is the method of example(s) 7, wherein calculating the reference dose using the chest size includes applying the chest size to a reference dose model, and wherein the reference dose model is based on experimental data from a smaller subject and a larger subject, wherein the smaller subject is smaller than the chest size and the larger subject is larger than the chest size.

Example 9 is the method of example(s) 8, wherein calculating the reference dose further comprises determining a first noise threshold for the smaller subject and a second noise threshold for the larger subject, and wherein applying the chest size to the reference dose model further includes applying the first noise threshold and the second noise threshold.

Example 10 is the method of example(s) 9, wherein determining the reference dose includes applying the formula $$CTDI_{vol,ref}(L) = CTDI_{vol}(L_0) = \frac{e^{2\alpha(L-L_0)}}{\left[L_{max} - L + \frac{T_{max}}{T_0}(L-L_0)\right] / (L_{max} - L_0)]^2}$$

where L is the chest size, $L_{max}$ is a size of the larger subject, $L_0$ is a size of the smaller subject, $T_{max}$ is the second noise threshold, $T_0$ is the first noise threshold, and $\alpha$ is a constant.

Example 11 is the method of example(s) 1-10, wherein driving the medical scanner comprises generating radiation at the radiation source and directing the radiation through target tissue.

Example 12 is the method of example(s) 11, wherein the target tissue comprises calcifications in a coronary artery.

Example 13 is the method of example(s) 1-12, further comprising: receiving scanner data associated with driving the medical scanner using the target peak kilovoltage and the dose parameters; and scaling the scanner data based on the target peak kilovoltage.

Example 14 is the method of example(s) 13, further comprising analyzing the scaled scanner data using standard Hounsfield unit thresholds to calculate an Agatston score associated with the scanner data.

Example 15 is the method of example(s) 14, wherein the standard Hounsfield unit (HU) thresholds comprise a first threshold of 0-129 HU associated with a score of 0, a second threshold of 130-199 HU associated with a score of 1, a third threshold of 200-299 HU associated with a score of 2, a third threshold of 300-399 HU associated with a score of 3, and a fourth threshold of 400 HU or greater associated with a score of 4.

Example 16 is the method of example(s) 13-15, wherein scaling the scanner data comprises: determining a scaling factor using the target peak kilovoltage; and scaling each pixel of the scanner data by the scaling factor.

Example 17 is the method of example(s) 16, wherein determining the scaling factor comprises applying the target peak kilovoltage to a lookup table.

Example 18 is the method of example(s) 16 or 17, wherein the scaling factor is at or approximately 1.59 when the peak kilovoltage is 70 kV, wherein the scaling factor is at or approximately 1.38 when the peak kilovoltage is 80 kV, wherein the scaling factor is at or approximately 1.24 when the peak kilovoltage is 90 kV, and wherein the scaling factor is at or approximately 1.14 when the scaling factor is 100 kV.

Example 19 is a method for pre-processing data for coronary calcium scoring, the method comprising: receiving scanner data associated with driving a computed tomography (CT) scanner at a target peak kilovoltage below 120 kV; determining a scaling factor using the target peak kilovoltage; scaling each pixel of the scanner data by the scaling factor; and outputting the scaled scanner data, wherein the scaled scanner data is analyzable using standard Hounsfield unit thresholds to calculate an Agatston score associated with the scanner data.

Example 20 is the method of example(s) 19, wherein the standard Hounsfield unit (HU) thresholds comprise a first threshold of 0-129 HU associated with a score of 0, a second threshold of 130-199 HU associated with a score of 1, a third threshold of 200-299 HU associated with a score of 2, a third threshold of 300-399 HU associated with a score of 3, and a fourth threshold of 400 HU or greater associated with a score of 4.

Example 21 is the method of example(s) 19 or 20, wherein the scaling factor is at or approximately 1.59 when the peak kilovoltage is 70 kV, wherein the scaling factor is at or approximately 1.38 when the peak kilovoltage is 80 kV, wherein the scaling factor is at or approximately 1.24 when the peak kilovoltage is 90 kV, and wherein the scaling factor is at or approximately 1.14 when the scaling factor is 100 kV.

Example 22 is a method for measuring cardiac health, the method comprising: determining a noise threshold $\sigma_t$ for a scan, the noise threshold $\sigma_t$ being based at least in part on a size of the subject; determining an optimal dose $CTDI_{vol,opt}$ based at least in part on the noise threshold $\sigma_t$; and determining dose parameters based at least in part on the optimal dose $CTDI_{vol,opt}$.

Example 23 is the method of example(s) 22, wherein the noise threshold $\sigma_t$ is based at least in part on the size of the subject relative to one or more threshold sizes.

Example 24 is the method of example(s) 23, wherein the noise threshold $\sigma_t$ is based at least in part on the size of the subject relative to a first threshold size and a second threshold size.

Example 25 is the method of example(s) 24, wherein the size of the subject is an effective diameter of a chest of the subject, the first threshold size is 30 centimeters, and the second threshold size is 36 centimeters.

Example 26 is the method of example(s) 25, wherein the noise threshold $\sigma_t$ has a first value if the size of the subject is less than or equal to the first threshold size, a second value if the size of the subject is greater than or equal to the first threshold size and less than or equal to the second threshold size, and a third value if the size of the subject is greater than the second threshold size.

Example 27 is the method of example(s) 24-26, wherein determining the noise threshold $\sigma_t$ includes applying the formula $$\sigma_t = \begin{cases} \sigma_{t1}, & \text{if } d_h \leq d_{h1} \\ Ke^{\lambda D_h}, & \text{if } d_{h1} \leq d_h \leq d_{h2} \\ Ke^{\lambda D_h}\text{(option 1)}, & \text{if } d_h > d_{h2} \\ \sigma_{t2}\text{(option 2)}, & \text{if } d_h > d_{h2} \end{cases},$$

where K and $\lambda$ are constants with known values, $d_{h1}$ is the first threshold size, $d_{h2}$ is the second threshold size, and $d_h$ is the size of the subject.

Example 28 is the method of example(s) 22-27, wherein determining the optimal dose $CTDI_{vol,opt}$ includes applying the formula $$CTDI_{vol,opt} = \left(\frac{Ae^{Bq(D_h)}}{\sigma_t}\right)^{-\frac{1}{C}},$$

where A, B, and C are constants with known values, and $q(D_h)$ is a function that represents the size of the of the subject relative to a reference size.

Example 29 is the method of example(s) 22-28, wherein the medical scan is used to determine a coronary artery calcium score for the subject.

Example 30 is the method of example(s) 22-29, further comprising driving a medical scanner using the dose parameters and a peak kilovoltage of 120 kV to perform the medical scan.

Example 31 is the method of example(s) 30, wherein the dose parameters include a tube current and an exposure time.

Example 32 is the method of example(s) 30 or 31, wherein the medical scanner is a computed tomography (CT) scanner.

Example 33 is a system comprising: a control system including one or more processors; and a memory having stored thereon machine readable instructions; wherein the control system is coupled to the memory, and the method of any one of example(s)s 1 to 32 is implemented when the machine executable instructions in the memory are executed by at least one of the one or more processors of the control system.

Example 34 is a system for assessing coronary artery calcification, the system including a control system configured to implement the method of any one of example(s)s 1 to 32.

Example 35 is a computer program product comprising instructions which, when executed by a computer, cause the computer to carry out the method of any one of example(s) 1 to 32.

Example 36 is the computer program product of example(s) 35, wherein the computer program product is a non-transitory computer readable medium.

What is claimed is:

1. A method for measuring cardiac health of a subject, the method comprising: determining a target peak kilovoltage for driving a radiation source of a medical scanner, wherein the target peak kilovoltage is less than 120 kV; calculating a reference dose based on a size of the subject relative to at least a larger reference subject and a smaller reference subject, the reference dose being associated with a peak kilovoltage of 120 kV; determining an appropriate dose by applying a reducing factor to the reference dose, wherein delivering the appropriate dose by driving the radiation source with the target peak kilovoltage achieves a contrast-to-noise ratio equal to a contrast-to-noise ratio achieved when delivering the reference dose by driving the radiation source with the peak kilovoltage of 120 kV; and determining dose parameters based on the appropriate dose.

2. The method of claim 1, wherein the target peak kilovoltage is at or between 70 kV and 100 kV.

3. The method of claim 1, wherein a value of the reducing factor is based on the target peak kilovoltage.

4. The method of claim 1, wherein the size of the subject is a chest size of the subject, wherein calculating the reference dose using the chest size of the subject includes applying the chest size of the subject to a reference dose model, and wherein the reference dose model is based on experimental data from a smaller subject and a larger subject, wherein the smaller subject has a chest size that is smaller than the chest size of the subject and the larger subject has a chest size that is larger than the chest size of the subject.

5. The method of claim 4, wherein calculating the reference dose further comprises determining a first noise threshold for the smaller reference subject and a second noise threshold for the larger reference subject, and wherein applying the chest size of the subject to the reference dose model further includes applying the first noise threshold and the second noise threshold.

6. The method of claim 5, wherein determining the reference dose includes applying the formula $$CTDI_{vol,ref}(L) = CTDI_{vol}(L_0) = \frac{e^{2\alpha(L-L_0)}}{\left[L_{max} - L + \frac{T_{max}}{T_0}(L - L_0)\right] / (L_{max} - L_0)\right]^2},$$

where L is the chest size of the subject, $L_{max}$ is the chest size of the larger reference subject, $L_0$ is the chest size of the smaller reference subject, $T_{max}$ is the second noise threshold, $T_0$ is the first noise threshold, and $\alpha$ is a constant.

7. The method of claim 1, further comprising:
receiving scanner data associated with driving the medical scanner using the target peak kilovoltage and the dose parameters;
determining a scaling factor using the target peak kilovoltage; and
scaling each pixel of the scanner data by the scaling factor.

8. A method for measuring cardiac health of a subject, the method comprising:
determining a noise threshold $\sigma_t$ for a scan performed using a medical scanner, the noise threshold $\sigma_t$ being based at least in part on a size of the subject relative to at least a first threshold size and a second threshold size;
determining an optimal dose $CTDI_{vol,opt}$ based at least in part on the noise threshold $\sigma_t$; and
determining dose parameters based at least in part on the optimal dose $CTDI_{vol,opt}$.

9. The method of claim 8, wherein the size of the subject is an effective diameter of a chest of the subject.

10. The method of claim 8, wherein the size of the subject is an effective diameter of a chest of the subject, the first threshold size is 30 centimeters, and the second threshold size is 36 centimeters.

11. The method of claim 8, wherein the noise threshold $\sigma_t$ has a first value if the size of the subject is less than or equal to the first threshold size, a second value if the size of the subject is greater than or equal to the first threshold size and less than or equal to the second threshold size, and a third value if the size of the subject is greater than the second threshold size.

12. The method of claim 8, wherein determining the noise threshold $\sigma_t$ includes applying the formula $$\sigma_t = \begin{cases} \sigma_{t1}, & \text{if } D_h \leq d_{h1} \\ Ke^{\lambda D_h}, & \text{if } d_{h1} \leq D_h \leq d_{h2} \\ Ke^{\lambda D_h} \text{(option 1)}, & \text{if } D_h > d_{h2} \\ \sigma_{t2} \text{(option 2)}, & \text{if } D_h > d_{h2} \end{cases},$$

where K and $\lambda$ are constants with known values, $d_{h1}$ is the first threshold size, $d_{h2}$ is the second threshold size, and $D_h$ is the size of the subject.

13. The method of claim 8, wherein the medical scanner is a computed tomography (CT) scanner.

14. The method of claim 8, wherein the dose parameters include at least a tube current, at least an exposure time, or at least both.

15. The method of claim 1, wherein the medical scanner is a computed tomography (CT) scanner.

16. The method of claim 1, wherein the dose parameters include at least a tube current, at least an exposure time, or at least both.

17. A method for measuring cardiac health of a subject, the method comprising:
determining a noise threshold $\sigma_t$ for a scan performed by a medical scanner, the noise threshold $\sigma_t$ being based at least in part on a size of the subject;
determining an optimal dose $CTDI_{vol,opt}$ by applying the formula $$CTDI_{vol,opt} = \left(\frac{Ae^{Bq(D_h)}}{\sigma_t}\right)^{-\frac{1}{C}},$$

where A, B, and C are constants with known values, and $q(D_h)$ is a function that represents the size of the of the subject relative to a reference size; and
determining dose parameters based at least in part on the optimal dose $CTDI_{vol,opt}$.

18. The method of claim 17, wherein the size of the subject is a chest size of the subject.

19. The method of claim 17, wherein the medical scanner is a computed tomography (CT) scanner.

20. The method of claim 17, wherein the dose parameters include at least a tube current, at least an exposure time, or at least both.

* * * * *